US007399469B2

(12) United States Patent
Zhang et al.

(10) Patent No.: US 7,399,469 B2
(45) Date of Patent: Jul. 15, 2008

(54) ANTI-LFL2 ANTIBODIES FOR THE DIAGNOSIS, PROGNOSIS AND TREATMENT OF CANCER

(75) Inventors: Yongke Zhang, Palo Alto, CA (US); Vanitha Ramakrishnan, Belmont, CA (US); Debbie Law, San Francisco, CA (US)

(73) Assignee: PDL BioPharma, Inc., Redwood City, CA (US)

( * ) Notice: Subject to any disclaimer, the term of this patent is extended or adjusted under 35 U.S.C. 154(b) by 369 days.

(21) Appl. No.: 11/089,872

(22) Filed: Mar. 25, 2005

(65) Prior Publication Data

US 2005/0260212 A1 Nov. 24, 2005

Related U.S. Application Data

(60) Provisional application No. 60/557,440, filed on Mar. 26, 2004, provisional application No. 60/638,708, filed on Dec. 22, 2004.

(51) Int. Cl.
*A61K 39/395* (2006.01)

(52) U.S. Cl. .............. 424/131.1; 424/130.1; 424/133.1; 424/138.1; 530/387.1; 530/387.2; 530/387.3; 530/387.7

(58) Field of Classification Search .............. 424/131.1, 424/130.1, 133.1, 138.1; 530/387.1, 387.2, 530/387.3, 387.7
See application file for complete search history.

(56) References Cited

U.S. PATENT DOCUMENTS

2005/0106644 A1* 5/2005 Cairns et al. ............... 435/7.23
2005/0239700 A1* 10/2005 Kloetzer et al. ............... 514/12

FOREIGN PATENT DOCUMENTS

WO WO-01/81363 A1 11/2001
WO WO 02/081518 10/2002
WO WO 03/024392 3/2003

OTHER PUBLICATIONS

Lederman et al. Molecular Immunology 28:1171-1181, 1991.*
Li et al. Proc. Natl. Acad. Sci. USA 77:3211-3214, 1980.*
Byers, T. CA Journal, vol. 49, No. 6, Nov./Dec. 1999.*
Gura. Science, v278, 1997, pp. 1041-1042.*
Bellone et al. Immunology Today, v20 (10), 1999, pp. 457-462.*
Satoh et al., "A Novel Member of the Leucine-Rich Repeat Superfamily Induced in Rat Astrocytes by β-amyloid", Biochemical and Biophysical Research Communications, vol. 290, pp. 756-762 (2002).
Reynolds et al., "Identification of a DNA-binding site and transcriptional target for EWS-WT1(+KTS) oncoprotein", Genes & Development, vol. 17, pp. 2094-2107 (2003).

* cited by examiner

*Primary Examiner*—David J. Blanchard
*Assistant Examiner*—Parithosh K. Tungaturthi

(57) ABSTRACT

Particular anti-LFL2 antibody compositions are provided herein. These antibodies may be used for diagnosis, prognosis, therapeutic monitoring and treatment of cancer, especially breast cancer, head/neck cancer, lung cancer, ovarian cancer, stomach cancer and pancreatic cancer. Furthermore, anti-LFL2 antibodies are provided herein which target the LFL2 stump remaining after proteolytic cleavage of the extracellular domain of LFL2. Additionally, anti-LFL2 antibodies are provided herein which target the stroma surrounding cancer tumors, wherein said stroma-targeting anti-LFL2 antibodies disrupt the integrity of the stroma surrounding the cancer tumor, and also make the stroma more permeable to chemotherapeutic agents and other molecular drug agents that target tumor cells.

10 Claims, No Drawings

ANTI-LFL2 ANTIBODIES FOR THE DIAGNOSIS, PROGNOSIS AND TREATMENT OF CANCER

CROSS REFERENCE TO RELATED APPLICATIONS

This application claims priority from U.S. Provisional Application Nos. 60/557,440 filed Mar. 26, 2004, and 60/638,708, filed Dec. 22, 2004, each of which is hereby incorporated by reference in its entirety.

FIELD OF THE INVENTION

The invention relates to the identification and generation of antibodies that specifically bind to LFL2 proteins, and to the use of such antibodies and compositions comprising them in the diagnosis, prognosis and therapy of cancer.

BACKGROUND OF THE INVENTION

Cancer is a major cause of morbidity in the United States. Cancers share the characteristic of disordered control over normal cell division, growth and differentiation. Their initial clinical manifestations are extremely heterogeneous, with over 70 types of cancer arising in virtually every organ and tissue of the body. Moreover, some of those similarly classified cancer types may represent multiple different molecular diseases. Unfortunately, some cancers may be virtually asymptomatic until late in the disease course, when treatment is more difficult and prognosis grim.

Treatment for cancer typically includes surgery, chemotherapy, immunotherapy and/or radiation therapy. Although nearly 50 percent of cancer patients can be effectively treated using these methods, the current therapies all induce serious side effects, which diminish quality of life. The identification of novel therapeutic targets and diagnostic markers will be important for improving the diagnosis, prognosis, and treatment of cancer patients.

Antigens suitable for immunotherapeutic strategies should be highly expressed in cancer tissues, preferably accessible from the vasculature and at the cell surface, and ideally not expressed in normal adult tissues. Expression in tissues that are dispensable for life, however, may be tolerated, e.g., reproductive organs, especially those absent in one sex. Therefore, provided herein is a protein that can be used as a biomarker and methods that can be used in diagnosis, prognosis and therapeutic monitoring of cancer and cancer patients, as well as therapeutic treatment of cancer patients.

Research in solid tumors has focused primarily on identifying targets and biomarkers present in the in the cancer epithelia. Very few strategies have focused on identifying genes up-regulated in the stroma that surrounds cancer tumors. Studies have shown that stromal-derived growth factors, stroma-produced extracellular matrix and/or the interaction of cancer epithelia with specific stromal cell antigens are important for tumorigenesis (Clamps et al. Proc. Natl. Acad. Sci USA 87: 75-79, 1990, Olumi et al., Cancer Res., 59: 5002-5011, 1999; Elenbaas et al., Genes Dev., 15: 50-65, 2001; Tuxhom et al., Cancer Res. 62:3298-3307, 2002). Cancer therapy, therefore, includes targeted therapies towards the tumor-associated stroma and their factors. Effective therapy targets the activated stroma during the proliferation stage. This results in preventing the stroma from producing a protumor microenvironment. The loss of this vital nutrient and growth factor supply line to the tumor cells ultimately results in tumor cell death. One such target for targeting the stroma is antibodies to the full length LFL2 protein and fragments thereof. LFL2 (also referred to in the literature as Lib and LRRC15) is a member of the leucine-rich repeat superfamily of proteins. LFL2 is a type I transmembrane protein with an extracellular domain that contains fifteen leucine-rich repeats. The full-length amino acid sequence of LFL2 is depicted in SEQ ID NO:1. The LFL2 gene is identical to LRRC15 ("leucine rich repeat containing 15") (Satoh, et al., Biochem. Biophys. Res. Commun., 2002; 290:756-62; Reynolds et al., Genes Dev., 2003; 17:2094-107; WO 01/81363, see, sequence id numbers 4 (DNA) and 43 (protein); and WO 02/081518, see, sequence id numbers 75 (DNA) and 76 (protein)) whose nucleic acid and amino acid sequences can be identified by Genbank Accession Nos. NM_130830.2 and NP_570843.1 respectively. The Unigene cluster identification number for LFL2/LRRC15 is Hs.288467 and the LocusLink ID is 131578. Satoh, et al. also describes RT-PCR and Northern blot data showing that LFL2 is strongly expressed in placental cells. High placental expression of LFL2 based on RT-PCR data was also disclosed in WO 01/81363 along with the general suggestion of cancer as one of several possible disease indications.

WO 02/081518 discloses RT-PCR expression data associating LFL2 with breast cancer, melanoma and brain cancer. WO 02/081518 also states that antibodies to these proteins can be generated for use in therapeutic and diagnostic methods.

WO 03/024392 discloses RT-PCR and DNA microarray results and concludes that LFL2 is upregulated in breast, uterine, colon, kidney, bladder, bone, ovarian and pancreatic tumor tissues. WO 03/024392 also reports GeneExpress® data and concludes that LFL2 is upregulated in stroma associated with bone, breast, colon, rectum, lung, ovarian, pancreas, soft tissue and bladder tumors. WO 03/024392 also reports in situ hybridization data and concludes that LFL2 expression occurs in a minority of sarcomas including synovial sarcoma, angiosarcoma, fibrosarcoma, gliosarcoma and malignant fibrohistiocytoma.

Furthermore, Reynolds et al. (Genes & Development 17: 2094-2107 (2003)) disclose LFL2 and describe RT-PCR, Northern blot and in situ hybridization data. Reynolds et al. observe that LFL2 is restricted to the cytotrophoblast layer, and, consequently, conclude that LFL2 may contribute to the invasiveness of breast cancer cells.

Expression of the rat ortholog of LFL2 is induced in rat C6 astrocytoma cells by pro-inflammatory cytokines (Satoh, et al., Biochem. Biophys. Res. Commun., 2002; 290:756-62). LFL2 expression is also induced by the presence of EWS-WT1(+KTS) (Reynolds et al., Genes Dev., 2003; 17:2094-107), a chimeric oncogene that is expressed in desmoplastic small round cell tumors (DSRCT). DSRCTs are soft tissue tumors that occur in primarily male children and young male adults. In this published report, expression of LFL2 in cancer cell lines was associated with breast cancer cell migration in vitro, suggesting a function of LFL2 in the aggressiveness and invasiveness of cancer.

Solid tumors often exhibit high interstitial fluid pressure (IFP), which causes poor uptake of anticancer drugs. While there are several mechanisms that regulate IFP in tumors, stroma-derived connective tissue control IFP by exerting a tension on the extracellular matrix/integrin. Agents known to reduce the tumor IFP have been shown to enhance the antitumor activity of chemotherapeutic agents (Griffon-Etienne et al., Cancer Res., 1999, 59:3776-82; Salnikov et al., FASEB J., 2003, 17:1756-8).

In spite of considerable research into for the molecular level mechanisms of cancer in general, cancer remains difficult to diagnose and treat effectively. Accordingly, there is a need in the art for improved methods for detecting and treating cancers. The present invention fulfills these needs and further provides other related advantages.

SUMMARY OF THE INVENTION

The present invention is directed to antibodies to the specific polypeptide target, LFL2, for diagnosis, prognosis, therapeutic intervention and therapeutic monitoring in cancers including breast, head/neck, lung, ovarian, stomach, pancreatic and other cancers.

The present invention is also directed to particular anti-LFL2 antibodies. One such antibody is designated herein as M25, comprising a heavy chain variable region (VH) with amino acid sequence depicted in SEQ ID NO:3 and a light chain variable region (VL) with amino acid sequence depicted in SEQ ID NO: 5. The VH nucleic acid sequence of the M25 antibody is depicted in SEQ ID NO: 2, and the VL nucleic acid sequence of the M25 antibody is depicted in SEQ ID NO: 4.

Another particular anti-LFL2 antibody provided by the present invention is designated herein as #139, which was deposited with the American Type Culture Collection (ATCC; Manassas, Va.) on Aug. 24, 2004 and assigned ATCC Deposit No. PTA-6163.

Another particular anti-LFL2 antibody provided by the present invention is designated herein as 1-19G12, which was deposited with the ATCC on Oct. 15, 2004 and assigned ATCC Deposit No. PTA-6256.

Another particular anti-LFL2 antibody provided by the present invention is designated herein as 1-13C3, which was deposited with the ATCC on Nov. 22, 2004 and assigned ATCC Deposit No. PTA-6330.

The present invention is also directed to anti-LFL2 antibodies that specifically bind to the same LFL2 epitope as any one of the anti-LFL2 antibodies selected from the group consisting of: M25, #139, 1-19G12 and 1-13C3.

The present invention is also directed to antibodies that specifically bind to the LFL2 "stub region," i.e., the region of LFL2 polypeptide that remains following proteolytic cleavage of LFL2 at the base of the extracellular region. The amino acid sequence of the LFL2 stub region (corresponding to amino acids 528-537 of SEQ ID NO:1) is depicted in SEQ ID NO: 6. In one embodiment, the invention provides antibodies that bind to the LFL2 stub region regardless of whether proteolytic cleavage has occurred. In another embodiment, the invention provides antibodies that only bind the stub region following proteolytic cleavage.

The present invention is also directed to a host cell which produces the M25 antibody, the #139 antibody, the 1-19G2 antibody or the 1-13C3 antibody.

The present invention is also directed to a method of inhibiting proliferation of cancer cells, comprising contacting the cancer cells with any of the particular anti-LFL2 antibodies designated as M25, #139, 1-19G12 and 1-13C3, or an antibody that binds to the same LFL2 epitope as bound by the anti-LFL2 antibodies designated as M25, #139, 1-19G12 and 1-13C3. In a preferred embodiment, the invention provides a method for inhibiting the proliferation of cancer cells wherein the cancer cells are selected from the group consisting of breast, head/neck, lung, ovarian, stomach and pancreatic cancers, as well as other cancer-associated LFL2-expressing cells.

The present invention is also directed to a method of detecting cancer cells in a biological sample from a patient, comprising contacting the biological sample with any of the particular anti-LFL2 antibodies designated as M25, #139, 1-19G12 and 1-13C3, or an antibody that binds to the same LFL2 epitope as bound by the anti-LFL2 antibodies designated as M25, #139, 1-19G12 and 1-13C3. In one preferred embodiment, the anti-LFL2 antibody specifically binds the stub region of the extracellular domain LFL2 corresponding to about amino acids 528-537 of the SEQ ID NO:1. In another embodiment, the LFL2 epitope detected is the shed extracellular domain of LFL2 corresponding to a polypeptide with amino acids 24-527 of SEQ ID NO:1.

The present invention is also directed to a method of monitoring progression of cancer in a patient, comprising detecting the level of a LFL2 polypeptide in a biological sample taken from the patient and comparing to the level of the LFL2 polypeptide in a biological sample taken from the patient at a later point in time, wherein an increase in the level of the LFL2 polypeptide indicates progression of the cancer. In one embodiment of the method, the level of LFL2 polypeptide is detected by detecting a polynucleotide in the sample, wherein the polynucleotide is an RNA equivalent of the nucleic acid sequence that encodes LFL2, or a polymorphic variant, allelic variant, mutant, interspecies homolog, or conservatively modified variant sequence at least 95% identical to the nucleic acid sequence that encodes LFL2. In another embodiment, the level of LFL2 polypeptide is detected by detecting the specific binding of an anti-LFL2 antibody to an LFL2 polypeptide. In one preferred embodiment, the LFL2 polypeptide detected is the stub region of the extracellular domain LFL2 corresponding to about amino acids 528-537 of the SEQ ID NO:1. In another embodiment, the LFL2 polypeptide detected is the shed extracellular domain of LFL2 corresponding to a polypeptide with amino acids 24-527 of SEQ ID NO:1.

The present invention is also directed to a method of monitoring the efficacy of treatment of a cancer in a patient, comprising detecting the level of a LFL2 polypeptide in a biological sample taken from the patient and comparing to the level of the LFL2 polypeptide in a biological sample taken from the patient at a later point in time, wherein a decrease in the level of the LFL2 polypeptide indicates efficacy of treatment of the cancer. In one embodiment of the method, the level of LFL2 polypeptide is detected by detecting a polynucleotide in the sample, wherein the polynucleotide is an RNA equivalent of the nucleic acid sequence that encodes LFL2, or a polymorphic variant, allelic variant, mutant, interspecies homolog, or conservatively modified variant sequence at least 95% identical to the nucleic acid sequence that encodes LFL2. In another embodiment, the level of LFL2 polypeptide is detected by detecting the specific binding of an anti-LFL2 antibody to an LFL2 polypeptide. In on preferred embodiment, the LFL2 polypeptide detected is the stub region of the extracellular domain LFL2 corresponding to about amino acids 528-537 of the SEQ ID NO:1. In another embodiment, the LFL2 polypeptide detected is the shed extracellular domain of LFL2 corresponding to a polypeptide with amino acids 24-527 of SEQ ID NO:1.

The present invention is also directed to a method of making the stroma of a cancer tumor more permeable to a chemotherapeutic agent, comprising contacting the stroma with any of the particular anti-LFL2 antibodies designated as M25, #139, 1-19G12 and 1-13C3, or any other antibody that binds to the same epitope as the particular anti-LFL2 antibodies designated as M25, #139, 1-19G12 and 1-13C3.

The present invention is also directed to the use of LFL2 target as a useful biomarker and/or therapeutic target in TGF-beta positive tumor cells.

DETAILED DESCRIPTION OF THE INVENTION

LFL2 as a Therapeutic Target

Applicants have discovered that LFL2 is highly expressed in cancer stroma of patient tumor samples. Using human cancer xenografts grown as subcutaneous tumors in mice as in vivo models for human disease, it has been demonstrated that murine LFL2 was highly expressed in the mouse stroma associated with the subcutaneous tumors. The in vivo expression of mouse LFL2 was induced by human cancer xenografts derived from human lung, ovarian, breast, colon and pancreatic cancers, but not by xenografts derived from human prostate cancer. In subsequent in vitro experiments, it was also demonstrated that LFL2 expression is induced in stromal cells/fibroblasts by co-culturing with epithelial cancer cell lines derived from the different types of cancers. The induction is specific and rapid (within hours of co-culturing). In addition, stimulation of stromal cells/fibroblasts with the growth-factor TGF-beta (transforming growth-factor-beta) also results in a significant induction of LFL2 expression. Thus, at least one of the mechanisms by which cancer cells induce the expression of LFL2 is via a TGF-beta-mediated signaling pathway.

LFL2 as a Biomarker

Applicants have discovered that the LFL2 amino acid sequence contains a proteolytic cleavage site at the base of the extracellular region. This proteolytic cleavage site is between amino acids 527 (arginine) and 528 (serine) in SEQ ID NO:1. Proteolytic cleavage of LFL2's extracellular domain (LFL2-ECD) results in the shedding of part of the LFL2-ECD, corresponding to about amino acids 24-527 of SEQ ID NO:1, into the blood stream. Following proteolytic cleavage of the LFL2-ECD, only a short polypeptide region referred to herein as the "stub region" remains on the cell surface. The 10 amino acid sequence of this stub region is depicted in SEQ ID NO:6. In in vitro experiments, shed LFL2-ECD is detected in tissue culture media when full-length LFL2 is over-expressed in fibroblastic cell lines. Approximately ⅓ of the LFL2 that is expressed and localized to the cell surface is shed. Over-expression of LFL2 will result in increased levels of shed LFL2-ECD in the blood stream. Thus, in addition to being a therapeutic target, LFL2 also represents a useful biomarker for the diagnosis and monitoring of numerous cancer indications, including soft tissue sarcomas, cancers of the lung, breast, head and neck, ovaries, stomach, colon and pancreas, and cancers that exhibit a significant TGF-beta signaling component.

Thus, LFL2 may be a useful biomarker and/or therapeutic target for TGF-beta positive tumor cells.

Therapeutic Agents that Target the LFL2 Stub Region Following Proteolytic Cleavage Additionally, because approximately ⅓ of expressed LFL2 localized on the cell surface is shed, leaving behind the stub region depicted in SEQ ID NO: 6, the most effective therapeutic antibodies targeting LFL2 are those that bind to both full-length, uncleaved LFL2, as well as to the stub region left behind following proteolytic cleavage. Accordingly, in a preferred embodiment, the therapeutic antibodies of the present invention comprise antibodies that bind both to both full-length, uncleaved LFL2, as well as to the stub region left behind following proteolytic cleavage.

Use of Anti-LFL2 Therapy to Augment Chemotherapy

Because LFL2 is expressed in the stroma surrounding the cancer tumor, targeting the tumor stroma via anti-LFL2 therapy can decrease the tumor interstitial fluid pressure (IFP), resulting in greater blood flow to the tumor and more efficient chemotherapeutic drug delivery or delivery of other molecular therapy that targets tumor cells. According to the present invention, anti-LFL2 therapy may be applied either prior to chemotherapy or other molecular therapy, concurrently with chemotherapy or other molecular therapy, and/or in an alternating treatment course with chemotherapy or other molecular therapy. Concurrent application includes the use of anti-LFL2 antibodies conjugated to chemotherapeutic effector moieties.

Another advantage of targeting the stroma surrounding a cancer tumor with anti-LFL2 antibodies is that, unlike the tumor cells of the cancer tumor, the chromosomes of the cells of the stroma are genetically stable as compared to the chromosomes of a cancer cell, which mutate regularly. Thus, unlike drug therapies that only target cancer cells, anti-LFL2 antibodies that target the stroma (as well as cancer cells) will have less chance of inducing drug resistance caused by mutations in cancer cells that result in loss of the target from the cancer cells, which typically occurs in chemotherapy that targets cancer cells only.

Anti-LFL2 Antibodies

The present invention provides high affinity antibodies for the human LFL2 protein. In one embodiment, the present invention provides particular anti-LFL2 antibodies. One such antibody is designated as M25, comprising a heavy chain variable region (VH) amino acid sequence depicted in SEQ ID NO: 3 and a light chain variable region (VL) amino acid sequence depicted in SEQ ID NO: 5. The VH nucleic acid sequence of the M25 antibody is depicted in SEQ ID NO: 2, and the VL nucleic acid sequence of the M25 antibody is depicted in SEQ ID NO: 4.

Another particular anti-LFL2 antibody provided by the present invention is designated as #139, which was deposited with the American Type Culture Collection (ATCC; Manassas, Va.) on Aug. 24, 2004 and assigned ATCC Deposit No. PTA-6163.

Another particular anti-LFL2 antibody provided by the present invention is designated as 1-19G12, which was deposited with the ATCC on Oct. 15, 2004 and assigned ATCC Deposit No. PTA-6256.

Another particular anti-LFL2 antibody provided by the present invention is designated as 1-13C3, which was deposited with the ATCC on Nov. 22, 2004 and assigned ATCC Deposit No. PTA-6330.

The present invention is also directed to other anti-LFL2 antibodies that bind to the same epitope of each of particular anti-LFL2 antibodies designated as M25, #139, 1-19G12 and 1-13C3.

Other selected antibodies that may be useful in this embodiment are disclosed in Table 1. The nucleotide and amino acid sequences of the $V_H$ and $V_L$ regions of the M25 antibody are disclosed in the attached sequence listing.

In some embodiments, the invention provides an antibody conjugated to an effector moiety or component. The effector moiety may be a label (e.g., a fluorescent label) or a cytotoxic agent (e.g., a radioisotope or a cytotoxic chemical). The invention provides a variety of cytotoxic agents that may be conjugated to an anti-LFL2 antibody including: diphtheria A chain, exotoxin A chain, ricin A chain, abrin A chain, curcin, crotin, phenomycin, neomycin and auristatin. In one preferred embodiment, the antibody of the present invention is conjugated to the cytotoxic agent auristatin E or auristatin F. In other embodiments the antibodies may be used alone to inhibit tumor cell growth. In another preferred embodiment of the invention, the naked anti-LFL2 antibody of the invention may be used to mediate antibody dependent cellular toxicity and thereby deliver a therapeutic effect.

The anti-LFL2 antibodies provided by the present invention include chimeric, humanized and human antibodies. In some embodiments, the invention provides primatized anti-LFL2 antibodies for treatment of primate patients. The present invention provides LFL2 antibodies that are whole antibodies, as well as anti-LFL2 antibody fragments, such as: Fab, Fab', $F(ab')_2$, Fv fragments, rIgG, diabodies, single chain antibodies, and multispecific antibodies.

In some embodiments, the LFL2 monoclonal antibody of the invention is chimeric, humanized or human monoclonal antibody. Preferably, the monoclonal antibody inhibits proliferation of tumor cells in vivo, wherein the tumor cells are selected from the group consisting of: breast, head/neck, lung, ovarian, stomach and pancreatic tumor, as well as other cancer-associated LFL2-expressing cells. In some embodiments, the monoclonal antibody is conjugated to an effector moiety, such as a cytotoxic agent (e.g. auristatin E or auristatin F). In an additional embodiment, the invention provides a monoclonal antibody that mediates antibody dependent cellular cytotoxicity (ADCC).

In another embodiment, the invention provides the host cells capable of producing any of the LFL2 antibody embodiments. In preferred embodiments, the host cell is selected from the group consisting of: NSO cells, Chinese Hamster Ovary (CHO) cells, *E. coli*, yeast cell, and insect cells.

The invention also provides pharmaceutical compositions comprising a pharmaceutically acceptable excipient and any of the anti-LFL2 antibody or antibody conjugate embodiments of the present invention.

The invention also provides methods of inhibiting proliferation of a cancer-associated cell. The method comprises contacting the cell with an LFL2 antibody of the invention. In most embodiments, the cancer cell is in a patient, typically a human. The patient may be diagnosed with and undergoing a therapeutic regimen to treat a solitary solid cancer tumor, a metastatic cancer, or may simply be suspected of having a cancer.

The present invention also provides methods of treatment using LFL2 and the associated composition embodiments. For example, the invention provides a method of inhibiting the growth of tumor cells comprising: administering to a mammal (preferably a human) a therapeutically effective amount of any anti-LFL2 antibody of the present invention. In preferred embodiments, the antibody of the method is conjugated to an effector moiety (e.g. auristatin E), or the antibody mediates antibody dependent cellular cytotoxicity. In a preferred embodiment, the invention provides a method for inhibiting the growth of tumor cells comprising a carcinoma selected from the group consisting of breast, head/neck, lung, ovarian, stomach and pancreatic cancers, as well as other cancer-associated LFL2-expressing cells.

In alternative embodiments of the method comprising administering an antibody and a therapeutically effective amount of a cytotoxic agent to a patient, the antibodies and cytotoxic agent may administered simultaneously, or either one before the other. In another alternative, the cytotoxic agent is conjugated to the antibody and thereby added simultaneously.

The invention further provides diagnostic tests and immunoassays employing a polynucleotide or polypeptide representative of the human LFL2 amino acid sequence or one of the LFL2 antibody embodiments of the present invention. In preferred embodiments, these methods involve detecting an LFL2-expressing cancer cell in a biological sample from a patient, or detecting the cleaved extracellular domain of LFL2, corresponding to about amino acids 24-527 of SEQ ID NO:1, in a blood or other body fluid sample from a patient. Detection may be carried out by detecting the LFL2 polynucleotide sequence (e.g. through hybridization), by detecting a LFL2 polypeptide sequence (e.g. by contacting the biological sample with an antibody of the invention), or via other methods of detecting specific sequences well-known in the art (e.g. PCR). In some embodiments, the antibody is conjugated to a label such as fluorescent label or radioisotope.

In one preferred embodiment, the invention provides a method of diagnosing a tumor in a mammal, comprising: contacting an anti-LFL2 antibody with a biological sample obtained from the mammal, and detecting the formation of a complex between the antibody and a polypeptide of the test sample; wherein the antibody binds a polypeptide comprising an amino acid sequence having at least 80% homology to the LFL2 amino acid sequence depicted in SEQ ID NO: 1, or the antibody binds the polypeptide comprising the amino acid sequence of the cleaved extracellular domain of LFL2, corresponding to about amino acids 24-527 of SEQ ID NO:1. In preferred embodiments of this method, the test sample is obtained from an individual suspected of having neoplastic cell growth or proliferation, or from an individual suspected of having cancer. In one embodiment the method further includes comparing the level of expression of the LFL2 gene product in the patient sample with the level of expression of LFL2 gene product in a biological sample taken from an individual that does not have cancer.

The present invention also provides a method of monitoring cancer progression or regression in an individual comprising measuring the level of expression of an LFL2 gene product, e.g. the LFL2 amino acid sequence depicted in SEQ ID NO: 1, or an mRNA equivalent of a polynucleotide sequence encoding SEQ ID NO:1, in a biological sample from said individual, wherein an increase in the expression level of the LFL2 gene product indicates a progression of the cancer, while a decrease in the expression level of the LFL2 gene product indicates a regression of the cancer.

In a preferred embodiment, the invention provides a method for detection of TGFβ1 induced cells in an individual comprising measuring the level of a LFL2 polypeptide in a biological sample from said individual, wherein the presence of the LFL2 polypeptide indicates the presence of TGFβ1 induced cells.

Definitions

As used herein, the term "antibody" refers to an immunoglobulin molecule that specifically binds to, or is immunologically reactive with, a particular antigen, and includes polyclonal, monoclonal, genetically engineered and otherwise modified forms of antibodies, including but not limited to chimeric antibodies, humanized antibodies, heteroconjugate antibodies (e.g., bispecific antibodies, diabodies, triabodies, and tetrabodies), and antigen binding fragments of antibodies, including e.g., Fab', $F(ab')_2$, Fab, Fv, rIgG, and scFv fragments. The term "scFv" refers to a single chain Fv antibody in which the variable domains of the heavy chain and the light chain from a traditional antibody have been joined to form one chain. In addition, the term "antibody," as used in the context of the invention disclosed herein encompasses mixtures of more than one antibody reactive with a specific antigen (e.g., a cocktail of different types of monoclonal antibodies reactive with LFL2).

References to "$V_H$" or a "VH" refer to the variable region of an immunoglobulin heavy chain of an antibody, including the heavy chain of an Fv, scFv, or Fab. References to "$V_L$" or a "VL" refer to the variable region of an immunoglobulin light chain, including the light chain of an Fv, scFv, dsFv or Fab.

An antibody having a constant region substantially identical to a naturally occurring class IgG antibody constant region refers to an antibody in which any constant region present is substantially identical, i.e., at least about 85-90%, and preferably at least 95% identical, to the amino acid sequence of the naturally occurring class IgG antibody's constant region.

The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced. Monoclonal antibodies useful with the present invention may be prepared using a wide variety of techniques known in the art including the use of hybridoma, recombinant, and phage display technologies, or a combination thereof. In many preferred uses of the present invention, including in vivo use of the LFL2 antibodies in humans for and in vitro detection assays, it may be preferable to use chimeric, primatized, humanized, or human antibodies.

A "chimeric antibody" is an immunoglobulin molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity. Methods for producing chimeric antibodies are known in the art.

The term "humanized antibody" or "humanized immunoglobulin" refers to an immunoglobulin comprising a human framework, at least one and preferably all complementarity determining regions (CDRs) from a non-human antibody, and in which any constant region present is substantially identical to a human immunoglobulin constant region, i.e., at least about 85-90%, and preferably at least 95% identical. Hence, all parts of a humanized immunoglobulin, except possibly the CDRs, are substantially identical to corresponding parts of one or more native human immunoglobulin sequences. Accordingly, such humanized antibodies are chimeric antibodies (U.S. Pat. No. 4,816,567), wherein substantially less than an intact human variable domain has been substituted by the corresponding sequence from a non-human species. Often, framework residues in the human framework regions will be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. See, e.g., Queen et al., U.S. Pat. Nos. 5,530,101; 5,585,089; 5,693,761; 5,693,762; 6,180,370 (each of which is incorporated by reference in its entirety). Antibodies can be humanized using a variety of techniques known in the art including, for example, CDR-grafting (EP 239,400; PCT publication WO 91/09967; U.S. Pat. Nos. 5,225,539; 5,530,101 and 5,585,089), veneering or resurfacing (EP 592,106; EP 519,596; Padlan, Mol. Immunol., 28:489-498 (1991); Studnicka et al., Prot. Eng. 7:805-814 (1994); Roguska et al., Proc. Natl. Acad. Sci. 91:969-973 (1994), and chain shuffling (U.S. Pat. No. 5,565,332), all of which are hereby incorporated by reference in their entireties.

Completely "human" antibodies may be desirable for therapeutic treatment of human patients. Human antibodies can be made by a variety of methods known in the art including phage display methods described above using antibody libraries derived from human immunoglobulin sequences. See U.S. Pat. Nos. 4,444,887 and 4,716,111; and PCT publications WO 98/46645; WO 98/50433; WO 98/24893; WO 98/16654; WO 96/34096; WO 96/33735; and WO 91/10741, each of which is incorporated herein by reference in its entirety. Human antibodies can also be produced using transgenic mice which are incapable of expressing functional endogenous immunoglobulins, but which can express human immunoglobulin genes., see, e.g., PCT publications WO 98/24893; WO 92/01047; WO 96/34096; WO 96/33735; European Patent No. 0 598 877; U.S. Pat. Nos. 5,413,923; 5,625,126; 5,633,425; 5,569,825; 5,661,016; 5,545,806; 5,814,318; 5,885,793; 5,916,771; and 5,939,598, which are incorporated by reference herein in their entireties. In addition, companies such as Abgenix, Inc. (Fremont, Calif.) and Medarex (Princeton, N.J.) can be engaged to provide human antibodies directed against a selected antigen using technology similar to that described above.

Completely human antibodies that recognize a selected epitope can be generated using a technique referred to as "guided selection." In this approach a selected non-human monoclonal antibody, e.g., a mouse antibody, is used to guide the selection of a completely human antibody recognizing the same epitope (Jespers et al., Biotechnology 12:899-903 (1988).

The term "primatized antibody" refers to an antibody comprising monkey variable regions and human constant regions. Methods for producing primatized antibodies are known in the art. See e.g., U.S. Pat. Nos. 5,658,570; 5,681,722; and 5,693,780, which are incorporated herein by reference in their entireties.

"Epitope" or "antigenic determinant" refers to a site on an antigen to which an antibody binds. Epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5 or 8-10 amino acids in a unique spatial conformation. Methods of determining spatial conformation of epitopes include, for example, x-ray crystallography and 2-dimensional nuclear magnetic resonance. Antibodies of "IgG class" refers to antibodies of IgG1, IgG2, IgG3, and IgG4. The numbering of the amino acid residues in the heavy and light chains is that of the EU index (Kabat, et al., "Sequences of Proteins of Immunological Interest", $5^{th}$ ed., National Institutes of Health, Bethesda, Md. (1991); the EU numbering scheme is used herein).

As used herein, the term "LFL2" refers to the full-length polypeptide with amino acid sequence SEQ ID NO:1, and also includes polypeptide polymorphic variants, alleles, conservatively modified variants, mutants, and interspecies homologues that: (1) have an amino acid sequence that has greater than about 60% sequence identity, 65%, 70%, 75%, 80%, 85%, 90%, or more preferably 91%, 92%, 93%, 94%, 95%, 96%, 97%, 98% or 99% or greater sequence identity, preferably over a region of at least about 25, 50, 100, 200 or more amino acids, to the amino acid sequence of SEQ ID NO:1; and/or (2) bind to antibodies, e.g., polyclonal antibodies, raised against an immunogen comprising an amino acid sequence of SEQ ID NO: 1, and conservatively modified variants thereof. Interspecies homologues of the LFL2 polypeptide sequence are typically from a mammal including, but not limited to, primate, e.g., human; rodent, e.g., rat, mouse, hamster; cow, pig, horse, sheep, or other mammal. A "LFL2 polypeptide" may include both naturally occurring or recombinant forms.

A "full length" LFL2 protein or nucleic acid refers to a polypeptide or polynucleotide sequence, or a variant thereof, that contains all of the elements normally contained in one or more naturally occurring, wild type LFL2 polynucleotide or polypeptide sequences. For example, a full length LFL2 nucleic acid will typically comprise all of the exons that encode for the full length, naturally occurring protein. The "full length" may be prior to, or after, various stages of post-translation processing or splicing, including alternative splicing.

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, preferably 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection (see, e.g., NCBI web site located at www.ncbi.nlm.nih.gov/BLAST/ or the like). Such sequences are then said to be "substantially identical." This definition also refers to, or may be applied to, the compliment of a test sequence. The definition also includes sequences that have deletions and/or additions, as well as those that have substitutions, as well as naturally occurring, e.g., polymorphic or allelic variants, and man-made variants. As described below, the preferred algorithms can account for gaps and the like. Preferably, identity exists over a region that is at least about 25 amino acids or nucleotides in length, or more preferably over a region that is 50-100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of one of the number of contiguous positions selected from the group consisting typically of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Preferred examples of algorithms that are suitable for determining percent sequence identity and sequence similarity include the BLAST and BLAST 2.0 algorithms. BLAST and BLAST 2.0 are used, with the parameters described herein, to determine percent sequence identity for the nucleic acids and proteins of the invention.

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, e.g., where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequences.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical or associated, e.g., naturally contiguous, sequences. Because of the degeneracy of the genetic code, a large number of functionally identical nucleic acids encode most proteins. For instance, the codons GCA, GCC, GCG, and GCU all encode the amino acid alanine. Thus, at every position where an alanine is specified by a codon, the codon can be altered to another of the corresponding codons described without altering the encoded polypeptide. Such nucleic acid variations are "silent variations," which are one species of conservatively modified variations. Every nucleic acid sequence herein which encodes a polypeptide also describes silent variations of the nucleic acid. One of skill will recognize that in certain contexts each codon in a nucleic acid (except AUG, which is ordinarily the only codon for methionine, and TGG, which is ordinarily the only codon for tryptophan) can be modified to yield a functionally identical molecule. Accordingly, often silent variations of a nucleic acid which encodes a polypeptide is implicit in a described sequence with respect to the expression product, but not with respect to actual probe sequences.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention. Typically conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)).

A "host cell" is a naturally occurring cell or a transformed cell that contains an expression vector and supports the replication or expression of the expression vector. Host cells may be cultured cells, explants, cells in vivo, and the like. Host cells may be prokaryotic cells such as *E. coli*, or eukaryotic cells such as yeast, insect, amphibian, or mammalian cells such as NSO, CHO, HeLa, and the like (see, e.g., the American Type Culture Collection catalog or web site, www.atcc.org).

The terms "isolated," "purified," or "biologically pure" refer to material that is substantially or essentially free from components that normally accompany it as found in its native state. Purity and homogeneity are typically determined using analytical chemistry techniques such as polyacrylamide gel electrophoresis or high performance liquid chromatography. A protein or nucleic acid that is the predominant species present in a preparation is substantially purified. In particular, an isolated nucleic acid is separated from some open reading frames that naturally flank the gene and encode proteins other than protein encoded by the gene. The term "purified" in some embodiments denotes that a nucleic acid or protein gives rise to essentially one band in an electrophoretic gel. Preferably, it means that the nucleic acid or protein is at least 85% pure, more preferably at least 95% pure, and most preferably at least 99% pure. "Purify" or "purification" in other embodiments means removing at least one contaminant from the composition to be purified. In this sense, purification does not require that the purified compound be homogenous, e.g., 100% pure.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers, those containing modified residues, and non-naturally occurring amino acid polymer.

The term "amino acid" refers to naturally occurring and synthetic amino acids, as well as amino acid analogs and amino acid mimetics that function similarly to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, e.g., an α carbon that is bound to a hydrogen, a carboxyl group, an amino group, and an R group, e.g., homoserine, norleucine, methionine sulfoxide, methionine methyl sulfonium. Such analogs may have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions similarly to a naturally occurring amino acid.

Amino acids may be referred to herein either by their commonly known three letter symbols or by the one-letter symbols recommended by the IUPAC-IUB Biochemical Nomenclature Commission. Nucleotides, likewise, may be referred to by their commonly accepted single-letter codes.

A "label" or a "detectable moiety" is a composition detectable by spectroscopic, photochemical, biochemical, immunochemical, chemical, or other physical means. For example, useful labels include fluorescent dyes, electron-dense reagents, enzymes (e.g., as commonly used in an ELISA), biotin, digoxigenin, colloidal gold, luminescent nanocrystals (e.g. quantum dots), haptens and proteins or other entities which can be made detectable, e.g., by incorporating a radiolabel into the peptide or used to detect antibodies specifically reactive with the peptide. The radioisotope may be, for example, $^{3}H$, $^{14}C$, $^{32}P$, $^{35}S$, or $^{125}I$. In some cases, particularly using antibodies against the proteins of the invention, the radioisotopes are used as toxic moieties, as described below. The labels may be incorporated into the LFL2 nucleic acids, proteins and antibodies at any position. Any method known in the art for conjugating the antibody to the label may be employed. The lifetime of radiolabeled peptides or radiolabeled antibody compositions may be extended by the addition of substances that stabilize the radiolabeled peptide or antibody and protect it from degradation. Any substance or combination of substances that stabilize the radiolabeled peptide or antibody may be used including those substances disclosed in U.S. Pat. No. 5,961,955.

An "effector" or "effector moiety" or "effector component" is a molecule that is bound (or linked, or conjugated), either covalently, through a linker or a chemical bond, or noncovalently, through ionic, van der Waals, electrostatic, or hydrogen bonds, to an antibody. The "effector" can be a variety of molecules including, e.g., detection moieties including radioactive compounds, fluorescent compounds, an enzyme or substrate, tags such as epitope tags, a toxin, activatable moieties, a chemotherapeutic or cytotoxic agent, a chemoattractant, a lipase; an antibiotic; or a radioisotope emitting "hard" e.g., beta radiation.

An antibody drug-conjugate (ADCs) is one approach for the treatment of cancer. (Braslawsky et al., Cancer Res, 1990; 50: 6608-14; Liu et al., Proc Natl Acad Sci USA, 1996; 93: 8618-23; Bernstein et al., Leukemia, 2000; 14: 474-5; Ross et al., Cancer Res, 2002; 62: 2546-53; Bhaskar et al., Cancer Res, 2003; 63: 6387-94; Doronina et al., Nat Biotechnol, 2003; 21: 778-84; Francisco et al., Blood, 2003; 102: 1458-65). The strategy of this approach is to deliver a toxic payload to the cancer cell via an antibody that targets a cancer-specific antigen. This strategy requires that the potent drug is internalized via the antibody-antigen complex, released within the cell and specifically kills the cancer cells (Bhaskar et al., Cancer Res, 2003; 63: 6387-94; Doronina et al., Nat Biotechnol, 2003; 21: 778-84; Francisco et al., Blood, 2003; 102: 1458-65). Ideally, the potent drug is internalized via the antibody-antigen complex, released within the cell and specifically kills the cancer cells. In order to minimize toxic side effects it is critical that the molecular target is not expressed in essential organs that are accessible to circulating antibodies. In addition, the target must be at the plasma membrane of cancer cells to allow antibody access.

The same criteria that make a target attractive for an ADC approach to cancer therapy are also desirable for an antibody dependent cellular cytotoxicity (ADCC) approach. In an ADCC approach, a naked antibody to the target is used to recruit immune effector cells (cytotoxic T lymphocytes, natural killer cells, activated macrophages) to the tumor. These effector cells then specifically kill the targeted tumor cells.

The term "cytotoxic agent" as used herein refers to a substance that inhibits or prevents the function of cells and/or causes destruction of cells. The term is intended to include radioactive isotopes (e.g., $I^{131}$, $I^{125}$, $Y^{90}$ and $Re^{186}$), chemotherapeutic agents, and toxins such as enzymatically active toxins of bacterial, fungal, plant or animal origin, or fragments thereof.

A "chemotherapeutic agent" is a chemical compound useful in the treatment of cancer. Examples of chemotherapeutic agents include adriamycin, doxorubicin, epirubicin, 5-fluorouracil, cytosine arabinoside ("Ara-C"), cyclophosphamide, thiotepa, busulfan, cytoxin, taxoids, e.g., paclitaxel (Taxol™, Bristol-Myers Squibb Oncology, Princeton, N.J.), and doxetaxel (Taxotere™, Rhone-Poulenc Rorer, Antony, France), toxotere, methotrexate, cisplatin, melphalan, vinblastine, bleomycin, etoposide, ifosfamide, mitomycin C, mitoxantrone, vincristine, vinorelbine, carboplatin, teniposide, daunomycin, carminomycin, aminopterin, dactinomycin, mitomycins, esperamicins (see U.S. Pat. No. 4,675,187), 5-FU, 6-thioguanine, 6-mercaptopurine, actinomycin D, VP-16, chlorambucil, melphalan, and other related nitrogen mustards. Also included in this definition are hormonal agents that act to regulate or inhibit hormone action on tumors such as tamoxifen and onapristone.

"Carriers" as used herein include pharmaceutically acceptable carriers, excipients, or stabilizers which are nontoxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids, antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming, counterions such as sodium; and/or nonionic surfactants such as TWEEN™, polyethylene glycol (PEG), and PLURONICS™.

A "therapeutically effective amount", in reference to the treatment of tumor, refers to an amount capable of invoking one or more of the following effects: (1) inhibition, to some extent, of tumor growth, including, slowing down and complete growth arrest; (2) reduction in the number of tumor cells; (3) reduction in tumor size; (4) inhibition (i.e., reduction, slowing down or complete stopping) of tumor cell infiltration into peripheral organs; (5) inhibition (i.e., reduction, slowing down or complete stopping) of metastasis; (6) enhancement of anti-tumor immune response, which may, but does not have to, result in the regression or rejection of the tumor; and/or (7) relief, to some extent, of one or more symptoms associated with the disorder. A "therapeutically effective amount" of a LFL2 antibody for purposes of treatment of tumor may be determined empirically and in a routine manner.

"Biological sample" as used herein is a sample of biological tissue or fluid that contains nucleic acids or polypeptides, e.g., of a LFL2 protein, polynucleotide or transcript. Such samples include, but are not limited to, tissue isolated from primates (e.g., humans), or from rodents (e.g., mice, and rats). Biological samples may also include sections of tissues such as biopsy and autopsy samples, frozen sections taken for histologic purposes, blood, plasma, serum, sputum, stool, tears, mucus, hair, skin, etc. Biological samples also include explants and primary and/or transformed cell cultures derived from patient tissues. A biological sample is typically obtained from a eukaryotic organism, most preferably a mammal such as a primate e.g., chimpanzee or human; cow; dog; cat; a rodent, e.g., guinea pig, rat, mouse; rabbit; or a bird; reptile; or fish.

"Providing a biological sample" means to obtain a biological sample for use in methods described in this invention. Most often, this will be done by removing a sample of cells from an animal, but can also be accomplished by using previously isolated cells (e.g., isolated by another person, at another time, and/or for another purpose), or by performing the methods of the invention in vivo. Archival tissues, having treatment or outcome history, will be particularly useful.

"Treatment" refers to both therapeutic treatment and prophylactic or preventative measures. Those in need of treatment include those already with the disorder as well as those in which the disorder is to be prevented.

A "patient" for the purposes of the present invention includes both humans and other animals, particularly mammals. Thus the methods are applicable to both human therapy and veterinary applications. In the preferred embodiment the patient is a mammal, preferably a primate, and in the most preferred embodiment the patient is human.

The phrase "specifically (or selectively) binds" to an antibody or "specifically (or selectively) immunoreactive with," when referring to a protein or peptide, refers to a binding reaction that is determinative of the presence of the protein, in a heterogeneous population of proteins and other biologics. Thus, under designated immunoassay conditions, the specified antibodies bind to a particular protein sequences at least two times the background and more typically more than 10 to 100 times background.

Specific binding to an antibody under such conditions requires an antibody that is selected for its specificity for a particular protein. For example, polyclonal antibodies raised to a particular protein, polymorphic variants, alleles, orthologs, and conservatively modified variants, or splice variants, or portions thereof, can be selected to obtain only those polyclonal antibodies that are specifically immunoreactive with LFL2 and not with other proteins. This selection may be achieved by subtracting out antibodies that cross-react with other molecules. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, Antibodies, A Laboratory Manual (1988) for a description of immunoassay formats and conditions that can be used to determine specific immunoreactivity).

The terms "cancer" and "cancerous" refer to or describe the physiological condition in mammals that is typically characterized by unregulated cell growth. Examples of cancer include but are not limited to, carcinoma, lymphoma, blastoma, sarcoma, and leukemia. More particular examples of such cancers include highest cancer, prostate cancer, colon cancer, squamous cell cancer, small-cell lunge cancer, non-small cell lunar cancer, gastrointestinal cancer, pancreatic cancer, glioblastoma cervical cancer, ovarian cancer, liver cancer, bladder cancer, hepatoma, colorectal cancer, endometrial carcinoma, salivary gland carcinoma kidney cancer, liver cancer, vulval cancer, thyroid cancer, hepatic carcinoma and various types of head and neck cancer.

"Tumor", as used herein, refers to all neoplastic cell growth and proliferation, whether malignant or benign, and all pre-cancerous and cancerous cells and tissues.

"Biomarker", as used herein, refers to a nucleic acid, peptide and/or protein that is present in biological fluids and/or tissues and that can be measured quantitatively. The quantitative analysis of a biomarker may be used to diagnose a specific condition (disease), monitor disease progression and/or monitor the efficacy of a therapeutic treatment. Also, the presence of a biomarker in a tissue and/or biological fluid may also be used to predict response of a patient with a specific condition (disease) to a specific therapeutic treatment, prior to the administration of the drug. Biomarker analysis may help define a patient population that is more likely to be responsive to a specific drug treatment. An example of this type of biomarker is the EGF receptor mutant that predicts responsiveness of 10% of non-small-cell lung cancer patients to the EGF receptor antagonist gefitinib (also known as IRESSA or ZD1839) Lynch et al., N Engl J. Med. 350:2129-2139, 2004.

Binding Affinity of Antibodies of the Invention

The antibodies of the invention specifically bind to LFL2 polypeptides. In preferred embodiments, the antibodies bind to LFL2 with very high affinity and exhibit $K_D$ values of less the 1 μM, preferably less than about 0.01 μM, and most preferably, 0.01 μM, or even subnanomolar.

In one embodiment, affinity of a LFL2 antibody may be determined by assaying competitive inhibition versus another LFL2 antibody (e.g. one of known affinity) for binding to a LFL2 polypeptide. Strong competitive inhibition indicates a strong binding affinity for LFL2.

Binding affinity for a target antigen is typically measured or determined by standard antibody-antigen assays, such as Biacore competitive assays, saturation assays, or immunoassays such as ELISA or RIA.

Such assays can be used to determine the dissociation constant of the antibody. The phrase "dissociation constant" refers to the affinity of an antibody for an antigen. Specificity of binding between an antibody and an antigen exists if the dissociation constant ($K_D$=1/K, where K is the affinity constant) of the antibody is <1 μM, preferably <100 nM, and most preferably <0.1 nM. Antibody molecules will typically have a $K_D$ in the lower ranges. $K_D$=[Ab−Ag]/[Ab][Ag] where [Ab] is the concentration at equilibrium of the antibody, [Ag] is the concentration at equilibrium of the antigen and [Ab−Ag] is the concentration at equilibrium of the antibody-antigen complex. Typically, the binding interactions between antigen and antibody include reversible noncovalent associations such as electrostatic attraction, Van der Waals forces and hydrogen bonds.

Antibody Drug-Conjugates of the Invention

The antibodies of the invention can be used in with drug conjugates. An antibody drug-conjugate (ADCs) is one approach for the treatment of cancer. (Braslawsky et al., Cancer Res, 1990; 50: 6608-14; Liu et al., Proc Natl Acad Sci USA, 1996; 93: 8618-23; Bernstein et al., Leukemia, 2000; 14: 474-5; Ross et al., Cancer Res, 2002; 62: 2546-53; Bhaskar et al., Cancer Res, 2003; 63: 6387-94; Doronina et al., Nat Biotechnol, 2003; 21: 778-84; Francisco et al., Blood, 2003; 102: 1458-65). The strategy of this approach is to deliver a toxic payload to the cancer cell via an antibody that targets a cancer-specific antigen. This strategy requires that the potent drug is internalized via the antibody-antigen complex, released within the cell and specifically kills the cancer cells (Bhaskar et al., Cancer Res, 2003; 63: 6387-94; Doronina et al., Nat Biotechnol, 2003; 21: 778-84; Francisco et al., Blood, 2003; 102: 1458-65). Ideally, the potent drug is internalized via the antibody-antigen complex, released within the cell and specifically kills the cancer cells. In order to minimize toxic side effects it is critical that the molecular target is not expressed in essential organs that are accessible to circulating antibodies. In addition, the target must be at the plasma membrane of cancer cells to allow antibody access.

The same criteria that make the LFL2 target attractive for an ADC approach to cancer therapy are also desirable for an antibody dependent cellular cytotoxicity (ADCC) approach. In an ADCC approach, a naked antibody to the target is used to recruit immune effector cells (cytotoxic T lymphocytes, natural killer cells, activated macrophages) to the tumor. These effector cells then specifically kill the targeted tumor cells.

Immunoassays

The antibodies of the invention can be used to detect LFL2 or LFL2 expressing cells using any of a number of well recognized immunological binding assays (see, e.g., U.S. Pat. Nos. 4,366,241; 4,376,110; 4,517,288; and 4,837,168). For a review of the general immunoassays, see also Methods in Cell Biology, Vol. 37, Asai, ed. Academic Press, Inc. New York (1993); *Basic and Clinical Immunology* 7th Edition, Stites & Terr, eds. (1991).

Thus, the present invention provides methods of detecting cells that express LFL2. In one method, a biopsy is performed on the subject and the collected tissue is tested in vitro. The tissue or cells from the tissue is then contacted with an anti-LFL2 antibody of the invention. Any immune complexes which result indicate the presence of a LFL2 protein in the biopsied sample. To facilitate such detection, the antibody can be radiolabeled or coupled to an effector moiety which is a detectable label, such as a radiolabel.

In another method, the cells may be detected in vivo using typical imaging systems. Then, the localization of the label is determined by any of the known methods for detecting the label. A conventional method for visualizing diagnostic imaging can be used. For example, paramagnetic isotopes can be used for MRI. Internalization of the antibody may be important to extend the life within the organism beyond that provided by extracellular binding, which will be susceptible to clearance by the extracellular enzymatic environment coupled with circulatory clearance.

LFL2 proteins can also be detected using standard immunoassay methods and the antibodies of the invention. Standard methods include, for example, radioimmunoassay, sandwich immunoassays (including ELISA), immunofluorescence assays, Western blot, affinity chromatography (affinity ligand bound to a solid phase), and in situ detection with labeled antibodies.

Suppression of Endogenous LFL2 Gene Expression through the Use of RNAi

In many species, introduction of double-stranded RNA (dsRNA) which may alternatively be referred to herein as small interfering RNA (siRNA), induces potent and specific gene silencing, a phenomena called RNA interference or RNAi. This phenomenon has been extensively documented in the nematode *C. elegans* (Fire, A., et al, Nature, 391, 806-811, 1998), but is widespread in other organisms, ranging from trypanasomes to mouse. Depending on the organism being discussed, RNA interference has been referred to as "co-suppression", "post-transcriptional gene silencing", "sense suppression" and "quelling".

RNAi is an attractive as a biotechnological tool because it provides a means for knocking out the activity of specific genes. It is particularly useful for knocking out gene expression in species that were not previously considered to be amenable to genetic analysis or manipulation.

In designing RNAi experiments there are several factors that need to be considered such as the nature of the dsRNA, the durability of the silencing effect, and the choice of delivery system.

To produce an RNAi effect, the dsRNA, or siRNA that is introduced into the organism should contain exonic sequences. Furthermore, the RNAi process is homology dependent, so the sequences must be carefully selected so as to maximize gene specificity, while minimizing the possibility of cross-interference between homologous, but not gene-specific sequences. Preferably the dsRNA exhibits greater than 90% or even 100% identity between the sequence of the dsRNA and the gene to be inhibited. Sequences less than about 80% identical to the target gene are substantially less effective. Thus, the greater homology between the dsRNA and the gene whose expression is to be inhibited, the less likely expression of unrelated genes will be affected.

In addition, the size of the dsRNA is important. Often dsRNA greater than 500 base pairs in length is used, however, smaller fragments can also produce an RNAi effect.

Introduction of dsRNA into can be achieved by any methods known in the art, including for example, microinjection or electroporation. A variety of mechanisms by which dsRNA may inhibit gene expression have been proposed, but evidence in support of any specific mechanism is lacking (Fire, A., 1999).

Compositions, Formulations and Administration of Anti-LFL2 Antibodies

The antibodies of the invention may be formulated in pharmaceutical compositions. Thus, the present invention also provides methods and compositions for administering a therapeutically effective dose of an anti-LFL2 antibody. The exact dose will depend on the purpose of the treatment, and will be ascertainable by one skilled in the art using well-known techniques (e.g., Ansel et al., *Pharmaceutical Dosage Forms and Drug Delivery*; Lieberman, Pharmaceutical Dosage Forms (vols. 1-3, 1992), Dekker, ISBN 0824770846, 082476918X, 0824712692, 0824716981; Lloyd, *The Art, Science and Technology of Pharmaceutical Compounding* (1999); and Pickar, *Dosage Calculations* (1999)).

The anti-LFL2 antibodies useful in the methods of the present invention may be used in an isolated and purified form and directly contacted with cancers cells or tumors. Methods of purifying antibodies are well-known in the art. Purity and homogeneity may be determined using standard analytical chemistry techniques such as polyacrylamide gel electrophoresis or high performance liquid chromatography. An antibody that is the predominant species present in a preparation is considered to be substantially purified. For example, antibody solution that exhibits essentially one band in an electrophoretic gel is substantially purified. Preferably, the antibody used in the pharmaceutical compositions of the invention is at least 85% pure, more preferably at least 95% pure, and most preferably at least 99% pure.

In preferred embodiments, the direct cancer cell killing method is carried out wherein the purified anti-LFL2 antibodies are formulated into a pharmaceutical composition that is administered to a subject in a therapeutically effective amount. As used herein, "therapeutically effective amount" refers to the amount of a pharmaceutical formulation or composition that is sufficient to cure, alleviate, attenuate or at least partially arrest the cancer and/or its symptoms, and/or complications. Clinical methods for determining the therapeutically effective amount of an anti-LFL2 antibody for treatment of cancer are well-known to those of ordinary skill in the art and may be determined empirically using routine experimentation. For example, in the context of cancer treatment, a "therapeutically effective amount" is an amount capable of invoking one or more of the following effects: (1) inhibition, to some extent, of cancer cell and/or tumor growth, including, slowing down and complete growth arrest; (2) reduction in the number of cancer cells; (3) reduction in tumor size; (4) inhibition (i.e., reduction, slowing down or complete stopping) of cancer cell infiltration into peripheral organs; (5) inhibition (i.e., reduction, slowing down or complete stopping) of cancer cell metastasis; (6) enhancement of anti-cancer immune response, which may, but does not have to, result in the regression or rejection of a tumor; and/or (7) relief, to some extent, of one or more symptoms associated with the disorder.

The pharmaceutical compositions for administration will commonly comprise an anti-LFL2 antibody dissolved in a pharmaceutically acceptable carrier or excipient, preferably an aqueous carrier. Acceptable carriers, excipients, or stabilizers, for the pharmaceutical composition are those which are nontoxic to the cell or mammal being exposed thereto at the dosages and concentrations employed. Examples of physiologically acceptable carriers include buffers such as phosphate, citrate, and other organic acids, antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrans; chelating agents such as EDTA; sugar alcohols such as mannitol or sorbitol; salt-forming, counter-ions such as sodium; and/or nonionic surfactants such as TWEEN®, polyethylene glycol (PEG), and PLURONICS™. A variety of aqueous carriers can be used, e.g., buffered saline and the like. These solutions should sterile and generally free of undesirable matter. The pharmaceutical compositions may be sterilized by conventional, well known sterilization techniques.

The pharmaceutical compositions also may contain pharmaceutically acceptable auxiliary substances as required to approximate physiological conditions such as pH adjusting and buffering agents, toxicity adjusting agents and the like, e.g., sodium acetate, sodium chloride, potassium chloride, calcium chloride, sodium lactate and other pharmaceutically acceptable salts, which is meant to include both acid and base addition salts. The pharmaceutical compositions may also include one or more of the following: carrier proteins such as serum albumin; buffers; fillers such as microcrystalline cellulose, lactose, corn and other starches; binding agents; sweeteners and other flavoring agents; coloring agents; and polyethylene glycol. The concentration of antibody in these formulations can vary widely, and will be selected primarily based on fluid volumes, viscosities, body weight and the like in accordance with the particular mode of administration selected and the patient's needs (e.g., "Remington's Pharmaceutical Science" (15th ed., 1980) and Goodman & Gillman, "The Pharmacologial Basis of Therapeutics" (Hardman et al., eds., 1996)).

In a preferred embodiment of the methods of the present invention, the anti-LFL2 antibody is formulated as a pharmaceutical composition comprising a solution of between about 1.0 mg/mL and 15.0 mg/mL antibody, about 15 mM to 30 mM citrate, about 125 mM to 175 mM Sodium Chloride, 0.04%-0.06% Polysorbate (TWEEN®) 80, at a pH of 5.5 to 7.5. Preferably, the pH range of the liquid formulation is between about pH 6.0 and pH 7.0, and most preferably between about pH 6.3 and pH 6.7. In other embodiments, the above anti-LFL2 antibody pharmaceutical composition may further comprise a chemotherapeutic agent, or alternatively, may be administered to a patient together with a pharmaceutically effective amount of another chemotherapeutic agent.

Preferably the liquid formulation of the pharmaceutical composition is a stable, colorless, or clear to slightly opalescent solution exhibiting no more than 10%, and preferably 5% or less of degaded antibody monomer as measured by SEC-HPLC. Preferably, no more than 10%, and preferably 5% or less of hydrolysis clipping is observed, and no more than 10%, and preferably 5% or less of antibody aggregation is formed. Preferably, the concentration, pH and osmolality of the formulation have no more than ±10% change. Potency is within 70-130%, preferably 80-120% of the control.

The administration of the pharmaceutical compositions comprising anti-LFL2 antibodies to a subject may be carried in a variety of ways, including, but not limited to, orally, subcutaneously, intravenously, intranasally, topically, transdermally, intraperitoneally, intramuscularly, intrapulmonary, vaginally, rectally, intraocularly, intraventricularly, or intrathecally. It is well recognized that antibodies when administered orally, should be protected from digestion. This is typically accomplished either by complexing the molecules with a composition to render them resistant to acidic and enzymatic hydrolysis, or by packaging the molecules in an appropriately resistant carrier, such as a liposome or a protection barrier. Means of protecting agents from digestion are well known in the art.

The pharmaceutical compositions may be administered in a variety of unit dosage forms depending upon the method of administration. For example, unit dosage forms suitable for oral administration include, but are not limited to, powder, tablets, pills, capsules and lozenges.

The exact dosage to be used in a particular embodiment of the method of the invention will depend on the purpose of the treatment, and may be ascertained by one skilled in the art using well-known techniques (e.g., Ansel et al., "Pharmaceutical Dosage Forms and Drug Delivery;" Lieberman, "Pharmaceutical Dosage Forms" (vols. 1-3, 1992), Dekker, ISBN 0824770846, 082476918X, 0824712692, 0824716981; Lloyd, "The Art, Science and Technology of Pharmaceutical Compounding" (1999); and Pickar, "Dosage Calculations" (1999)). As is known in the art, adjustments for cancer degradation, systemic versus localized delivery, and rate of new protease synthesis, as well as the age, body weight, general health, sex, diet, time of administration, drug interaction and the severity of the condition may be necessary, and will be ascertainable with routine experimentation by those skilled in the art.

In one embodiment of the methods of the present invention, a pharmaceutical compositions comprising an anti-LFL2 antibody is administered to a patient based on the weight of antibody (in mg) per patient body weight (in kg). Preferred dose levels include at least about 0.5 mg/kg, 1.0 mg/kg, 2.5 mg/kg, 5.0 mg/kg, 10.0 mg/kg, and 15 mg/kg. Preferably, the dose is administered to the patient as an intravenous infusion over 1 hour. Additional doses may be administered over an extended time period such that a steady state serum concentration is established in the patient. For example, an infusion of 10 mg/kg may be administered once a week over the course of a year.

In one preferred embodiment, the anti-LFL2 antibody dosing level and schedule are selected to ensure that the dose produces a maximum serum concentration below the safe mean peak serum concentrations seen in pharmacokinetic studies carried out in monkeys (e.g., cynomolgus).

In accordance with one embodiment of the methods of therapeutic cancer cell inhibition of the present invention, a pharmaceutical composition comprising an anti-LFL2 antibody is administered to a patient intravenously at a fixed dosage, typically about 0.1 to 10 mg per patient per day. In embodiments where the pharmaceutical composition is administered to a secluded site, such as into a body cavity or into a lumen of an organ, and not into the blood stream, fixed dosages from 0.1 mg up to about 100 mg per patient per day may be used. Substantially higher dosages are possible for embodiments where topical administration is desired. Actual methods for preparing parenterally administrable compositions will be known or apparent to those skilled in the art, e.g., "Remington's Pharmaceutical Science," and Goodman and Gillman, "The Pharmacologial Basis of Therapeutics," supra.

The pharmaceutical compositions employed in the methods of the present invention may be administered as part of a therapeutic or prophylactic treatment. In a therapeutic method, the pharmaceutical composition is administered to a patient already suffering from a cancer in an amount sufficient to cure, or at least partially arrest the progress of the disease and its complications. Generally, in a therapeutic treatment context, the progress of the therapy may be measured as decrease in tumor size or a decrease in the rate of tumor growth. An amount adequate to accomplish this is defined as a "therapeutically effective dose." Amounts effective for this use will depend upon the severity of the cancer and the general state of the patient's health. Single or multiple administrations of the pharmaceutical compositions may be employed depending on the dosage and frequency tolerated by the patient.

An early-stage treatment method is directed to preventing or slowing the development of cancer in a subject that is suspected of developing the disease, or in the very early stage of the disease. The particular dose required for an early-stage treatment will depend upon the medical condition and history of the patient, the particular cancer being prevented, as well as other factors such as age, weight, gender, administration route, efficiency, etc. An early-stage treatment method also may be used prophylactically, e.g., in a patient who has previously had cancer to prevent a recurrence of the cancer, or in a patient who is suspected of having a significant likelihood of developing cancer. For example, a patient with a genetic predisposition for breast cancer, in whom some pre-tumorous cancer marker has been detected (e.g., micro-metastases detected by PCR), will be particularly well-suited for the early-stage treatment method.

In an alternative embodiment of the present invention, the therapeutic methods may be carried out wherein a chemotherapeutic agent is administered in addition to the anti-LFL2 antibody. Typical chemotherapeutic agents useful in this embodiment are disclosed supra. This combination therapy method may be particularly preferred in an early-stage, or prophylactic treatment context where the patient lacks fully developed disease symptoms.

Detection of LFL2 for Diagnostic and Prognostic Applications

In one aspect, the RNA expression levels of genes are determined for different cellular states in the cancer phenotype. Expression levels of genes in normal tissue (e.g., not undergoing cancer) and in cancer tissue (and in some cases, for varying severities of cancer that relate to prognosis, as outlined below, or in non-malignant disease are evaluated to provide expression profiles. An expression profile of a particular cell state or point of development is essentially a "fingerprint" of the state of the cell. While two states may have any particular gene similarly expressed, the evaluation of a number of genes simultaneously allows the generation of a gene expression profile that is reflective of the state of the cell. By comparing expression profiles of cells in different states, information regarding which genes are important (including both up- and down-regulation of genes) in each of these states is obtained. Then, diagnosis may be performed or confirmed to determine whether a tissue sample has the gene expression profile of normal or cancerous tissue. This will provide for molecular diagnosis of related conditions.

"Differential expression," or grammatical equivalents as used herein, refers to qualitative or quantitative differences in the temporal and/or cellular gene expression patterns within and among cells and tissue. Thus, a differentially expressed gene can qualitatively have its expression altered, including an activation or inactivation, in, e.g., normal versus cancer tissue. Genes may be turned on or turned off in a particular state, relative to another state thus permitting comparison of two or more states. A qualitatively regulated gene will exhibit an expression pattern within a state or cell type which is detectable by standard techniques. Some genes will be expressed in one state or cell type, but not in both. Alternatively, the difference in expression may be quantitative, e.g., in that expression is modulated, either up-regulated, resulting in an increased amount of transcript, or down-regulated, resulting in a decreased amount of transcript. The degree to which expression differs need only be large enough to quantify via standard characterization techniques as outlined below, such as by use of Affymetrix GeneChip™ expression arrays. See, e.g., Lockhart (1996) *Nature Biotechnology* 14:1675-1680. Other techniques include, but are not limited to, quantitative reverse transcriptase PCR, northern analysis, and RNase protection. As outlined above, preferably the change in expression (e.g., up-regulation or down-regulation) is at least about 50%, more preferably at least about 100%, more preferably at least about 150%, more preferably at least about 200%, with from 300 to at least 1000% being especially preferred.

Evaluation may be at the gene transcript, or the protein level. The amount of gene expression may be monitored using nucleic acid probes to the DNA or RNA equivalent of the gene transcript, and the quantification of gene expression levels, or, alternatively, the final gene product itself (e.g., LFL2 protein) can be monitored, e.g., with antibodies to LFL2 and standard immunoassays (ELISAs, etc.) or other techniques, including mass spectroscopy assays, 2D gel electrophoresis assays, etc.

In one embodiment of a diagnostic method, nucleic acids encoding the LFL2 are detected. Although DNA or RNA encoding LFL2 may be detected, of particular interest are methods wherein an mRNA encoding LFL2 protein is detected. Probes to detect mRNA can be a nucleotide/deoxynucleotide probe that is complementary to and hybridizes with the mRNA and includes, but is not limited to, oligonucleotides, cDNA or RNA. Probes also should contain a detectable label, as defined herein. In one method the mRNA is detected after immobilizing the nucleic acid to be examined on a solid support such as nylon membranes and hybridizing the probe with the sample. Following washing to remove the non-specifically bound probe, the label is detected. In another method detection of the mRNA is performed in situ. In this method permeabilized cells or tissue samples are contacted with a detectably labeled nucleic acid probe for sufficient time to allow the probe to hybridize with the target mRNA. Following washing to remove the non-specifically bound probe, the label is detected. For example a digoxygenin labeled riboprobe (RNA probe) that is complementary to the mRNA encoding an LFL2 protein is detected by binding the digoxygenin with an anti-digoxygenin secondary antibody and developed with nitro blue tetrazolium and 5-bromo-4-chloro-3-indoyl phosphate. In one embodiment, LFL2 nucleic acid probes are attached to biochips as for detection and quantification of in a particular sample. PCR techniques may also be used to provide greater sensitivity.

In a preferred embodiment, various LFL2 proteins from are used in diagnostic assays. In a preferred embodiment, the expression of LFL2 is used, preferably in conjunction with high throughput screening techniques to allow simultaneous monitoring of other genes and/or corresponding polypeptides.

As described and defined herein, LFL2 proteins may be used as prognostic or diagnostic markers of cancer. Detection of these proteins in putative cancer tissue allows for detection, diagnosis, or prognosis of cancer, and for selection of therapeutic strategy. In one embodiment, antibodies are used to detect LFL2 proteins.

In another preferred method, antibodies to the LFL2 protein find use in in situ imaging techniques, e.g., in histology. See, e.g., Asai (ed. 1993) *Methods in Cell Biology: Antibodies in Cell Biology* (vol. 37) Academic Press. Cells are contacted with from one to many antibodies to the LFL2 protein. Following washing to remove non-specific antibody binding, the presence of the antibody or antibodies is detected. In one embodiment the antibody is detected by incubating with a secondary antibody that contains a detectable label. In another method the primary antibody to the LFL2 protein contains a detectable label, e.g., an enzyme marker that can act on a substrate. In another preferred embodiment each one of multiple primary antibodies contains a distinct and detectable label. This method finds particular use in simultaneous screening for a plurality of cancer proteins. As will be appreciated by one of ordinary skill in the art, many other histological imaging techniques are also provided by the invention.

In a preferred embodiment the label is detected in a fluorometer which has the ability to detect and distinguish emissions of different wavelengths. In addition, a fluorescence activated cell sorter (FACS) can be used in the method.

In another preferred embodiment, antibodies find use in diagnosing cancer from blood, serum, plasma, stool, and other samples. Such samples, therefore, are useful as samples to be probed or tested for the presence of LFL2 protein. Antibodies may be used to detect an LFL2 protein by previously described immunoassay techniques including ELISA, immunoblotting (western blotting), immunoprecipitation, BIACORE technology, and the like. Conversely, the presence of antibodies may indicate an immune response against an endogenous LFL2 protein.

In a preferred embodiment, in situ hybridization of labeled LFL2 nucleic acid probes to tissue arrays is done. For example, arrays of tissue samples, including cancer tissue and/or normal tissue, are made. In situ hybridization is then performed. When comparing the fingerprints between an individual and a standard, the skilled artisan can make a diagnosis, a prognosis, or a prediction based on the findings.

In a preferred embodiment, the LFL2 proteins, antibodies, nucleic acids, modified proteins and cells containing LFL2 sequences may be used in prognosis assays. As above, gene expression profiles can be generated that correlate to cancer, clinical, pathological, or other information, in terms of long term prognosis. Again, this may be done on either a protein or gene level, with the use of a plurality of genes being preferred. As above, LFL2 probes may be attached to biochips for the detection and quantification of LFL2 protein sequences in a tissue or patient. The assays proceed as outlined above for diagnosis. PCR method may provide more sensitive and accurate quantification.

Kits for Use in Diagnostic and/or Prognostic Applications

For use in diagnostic, research, and therapeutic applications suggested above, kits are also provided by the invention. In the diagnostic and research applications such kits may include any or all of the following: assay reagents, buffers, and LFL2-specific antibodies, or nucleic acid probes, of the invention. A therapeutic product may include sterile saline or another pharmaceutically acceptable emulsion and suspension base.

In addition, the kits may include instructional materials containing directions (i.e., protocols) for the practice of the methods of this invention. While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

The following examples are intended to illustrate but not limitat the invention disclosed herein.

EXAMPLES

Example 1

Gene Expression Analysis Shows LFL2 Up-Regulation in Various Cancer Tissues

DNA Microarray Analysis

Clinical patient tumor tissue from 54 breast cancers, 74 prostate cancers, 97 colon cancers, 103 non-small cell lung cancers, 126 ovarian cancers, 82 transitional cell carcinomas of the bladder, 22 head and neck cancers, 39 stomach cancers, 20 renal clear cell carcinomas, 47 pancreatic cancers, 26 soft tissue sarcomas and 347 samples of non-malignant adult tissues representing 77 different organs were collected and processed for gene expression profiling using Hu03, a customized Affymetrix GeneChip®, as previously published (Bhaskar et al., Cancer Res, 2003; 63: 6387-94; Henshall et al., Oncogene, 2003; 22: 6005-12; Henshall et al., Cancer Res, 2003; 63: 4196-203).

To identify cancer-associated genes, gene expression ratios of cancer samples to normal body tissues were calculated for all 59619 probe sets on the Hu03. After sorting all probe sets by ratio, genes with the highest cancer to normal adult tissue expression ratios were selected for further evaluation if their encoded sequences contained predicted transmembrane domains and/or other structural domains that suggested localization of the gene product to the plasma membrane. In addition, expression profiles of selected genes were examined in detail, such that a selected target must exhibit expression in at least 20% of tumor samples with a minimum 2 fold increase compared to the $85^{th}$ percentile of the 347 normal body tissues.

Real Time PCR Protocol and Probe Sequence

Real time PCR (polymerase chain reaction) was performed according to Applied Biosystems™ (AB) protocol in User Bulletin #2 (ABI Prism 7700™ Sequence Detection System). Detection of the PCR product was performed using AB Assay-On-Demand™ kit: Hs.00370056_s1 containing 25 ng of total RNA per sample. The FAM-labeled probe used to detect LFL2 message contains the following sequence:

```
5'-AGGTTCTGCCCATCGGCCTCTTCCA-3' (SEQ D NO:7).
```

Results

DNA microarray analysis showed that the LFL2 gene is up-regulated in a variety of cancer tissues relative to expression in normal tissues. LFL2 was selectively up-regulated in soft tissue sarcomas and in cancers of the lung, breast, head and neck, ovaries, stomach, colon and pancreas. In all cases, LFL2 overexpression was detected in 20-80% of tumor samples, depending on tissue of origin. More specifically, LFL2 was overexpressed in 80% of breast tumors, 61% of lung tumors (both adeno- and squamous cell carcinomas), 44% of gastric tumors, 21% of colon tumors, 73% of head and neck tumors, 35% of ovarian tumors, 36% of pancreatic tumors, and 42% of soft tissue sarcomas. The DNA microarray results were confirmed by real time PCR. No expression was detected in genitourinary cancers, including cancers of the prostate, bladder and kidney.

Example 2

Generation of Anti-LFL2 Antibodies

Cloning of Human and Murine LFL2

Total RNA was isolated from human lung cancer tissue using Trizol™ reagent (Invitrogen, Carlsbad, Calif.). cDNA was produced from 1 ug of total RNA using Superscript II (Invitrogen, Carlsbad, Calif.). The LFL2 cDNA was cloned from 50 ng of LNCaP cDNA using PCR containing AdvantageII™ polymerase (BD Biosciences™—Clontech™, Palo Alto, Calif.) and the following two outside primers: LFL2 RT 5'-ATGCCACTGAAGCATTATCTCCTTTTG (SEQ ID NO:8) and LFL2 RT 3' TGCTCCAGCCTGCCTCTTTAACAC (SEQ ID NO:9), followed by nested PCR using the cloning primers: LFL2 5'-TGGTTAATTAACATGCCACTGAAGCATTATCTCCTT (SEQ ID NO:10) and LFL2 3'-Fc-ATTGCGGCCGCCCCGCTCTGGCCTGGGTCAT (SEQ ID NO:11).

The products of this reaction were cloned into Pac I (5')/Not I (3') sites of a modified pBMN-Z-I-Blast vector (G. Nolan, Stanford University, CA), resulting in an in-frame fusion between the extracellular domain of the LFL2 gene and the constant region of the human gamma 1 immunoglobulin heavy chain gene.

Murine LFL2 was cloned by PCR from mouse skin and lung cDNA using the following 2 outside primers: Mu LFL2 5' RT ATGCTGCAGTCTTGAGCCGGTC (SEQ ID NO:12) and Mu LFL2 3' RT TTATGTGGCCCCAGGTTTGGAAG (SEQ ID NO:13), followed by nested PCR using the cloning primers: Mu LFL2 5' cloning AGGTTAATTAAGATGCCGCTGAAACATTATCTCC (SEQ ID NO:14) and Mu LFL2 3'Fc ATGCGGCCGCTTCGATGGTGTTTAGATCGGTGTAG (SEQ ID NO:15). Murine LFL2-Fc fusion was generated as described above for human LFL2.

Antibody Methods

Female Balb/c mice (Taconic Farms™, Germantown, Pa.) were immunized with LFL2-Fc fusion protein. Monoclonal antibodies (mAbs) were generated by standard techniques with spleen cells being fused to the P3X__63_Ag8.653 fusion partner (American Type Culture Collection—ATCC). A panel of LFL2 specific antibodies were identified using a variety of techniques including ELISA on LFL2 protein (human and murine LFL2-Fc), western blotting and FACS analysis on LFL2-expressing cell lines.

M25 Binding Affinity for Mouse and Human LFL2

Kinetics measurements between human LFL2-Fc fusion protein and anti-LFL2 mAbs were performed using BIAcore 3000™ (BIAcore™, Sweden). Anti-LFL2 mAbs were immobilized with 100 RUs on Research-grade CM5 sensor chip by the BIAcore amine coupling reagents (N-ethyl-N'-dimethylaminopropylcarbodiimide, EDC; N-hydroxysuccinimide, NHS; and ethanolamine HCl, pH8.5). Assays were run at a flow rate of 30 ul/min at room temperature. Three-minute association phase of each LFL2-Fc was followed by ten-minute injection of running buffer (10 mM Hepes, 300 mM sodium chloride, 3 mM EDTA, 0.05% P-20, pH7.4) to monitor dissociation. The mAb surface was regenerated with 25 mM NaOH. The binding kinetics of each LFL2-mAb pair was calculated from the data at six different concentrations (2048 nM, 512 nM, 128 nM, 32 nM, 8 nM, 2 nM) of LFL2-Fc analyte, using the BIAevaluate program. Double referencing was applied in each analysis to eliminate background responses from reference surface and buffer only control. The affinity ($K_D$) of binding was obtained by simultaneously fitting the association and dissociation phases of the sensorgram from the analyte concentration series using the bivalent analyte model from BIAevaluate software.

Results

To study LFL2 protein expression, monoclonal antibodies (mAbs) were generated by immunizing mice with an Fc fusion protein of the extracellular domain of human LFL2. From an initial pool of about one hundred hybridoma supernatants, a panel of anti-LFL2 supernatants were selected based on their ability to efficiently recognize LFL2 protein in a variety of techniques, including FACS, Western blotting, ELISA and immunohistochemistry (IHC). The panel of anti-LFL2 mAbs includes: #139, #192, M25, D23 and D26. D23 and D26 recognize denatured human LFL2 on Western blots. M25, #139 and #192 recognize native human LFL2 protein using ELISA, on live cells using FACS and in frozen human tissues using IHC. M25 also recognizes native murine LFL2 by ELISA, FACS and IHC. The isotypes of a panel of anti-LFL2 antibodies are shown in Table 1.

TABLE 1

Ig Isotypes of anti-LFL2 antibodies

| Antibody | Ig isotype |
|---|---|
| 139 | IgG 2a |
| 26 | IgG 2a |
| 192 | IgG 2a |
| 101 | IgG 2a |
| 173 | IgG 2a |
| 61 | IgG 2a |
| M25 | IgG 2a |
| D23 | IgG 2a |
| D11 | IgG 2a |
| 34 | IgG 1 |
| 57 | IgG 1 |
| 107 | IgG 1 |
| 166 | IgG 1 |
| D26 | IgG 1 |
| 25 | IgG 2a + 2b |
| D33 | IgG 1 + 2a + 2b |
| 1-13C3 | IgG 2b |
| 1-19G12 | IgG1 |

To further characterize anti-LFL2 mAbs, binding affinity ($K_D$), association ($k_a$) and dissociation ($k_d$) constants were determined by Biacore™ analysis. As shown below in Table 2, the mAbs M25 and 139a exhibit sub-nanomolar binding affinity for mouse and human LFL2, respectively.

TABLE 2

| mAb | $k_a$ | $K_d$ | $K_D$ |
|---|---|---|---|
| Human LFL2-Fc and mAbs binding affinity | | | |
| 139 | 1.77E+04 | 4.76E−06 | 2.75E−10 |
| 25a | 6.03E+04 | 2.64E−05 | 4.31E−10 |
| M8 | 2.19E+05 | 2.13E−04 | 9.89E−10 |
| M25 | 1.68E+05 | 1.89E−04 | 1.20E−09 |
| Mouse LFL2-Fc and mAbs binding affinity | | | |
| mAb | ka | Kd | KD |
| M25 | 1.71E+05 | 1.43E−04 | 8.70E−10 |
| M8 | equilibrium reached rapidly | | 1.29E−07 |
| 25a | | | no binding |

Example 3

Immunohistochemistry (IHC) Analysis of LFL2 Protein Expression in Cancer Patient Tumor Samples IHC Protocol Human normal and cancer tissue samples (Zoion™, Hawthorne, N.Y.) were frozen in OCT compound and stored at −70° C. Cryostat tissue sections (7 mm) were fixed in 75% acetone/25% ethanol for 1 minute. Tissue sections were incubated with either anti-LFL2 specific monoclonal antibody #192a (mAb) or control mouse IgG1 (TIB191, a mouse anti-trinitrophenol mAb (hybridoma clone 1B76.11, ATCC)) for 30 minutes. Antibody binding was detected using biotinylated secondary antibody (Goat-anti-mouse IgG (3 mg/ml, 30 minutes; Jackson ImmunoResearch™)), and developed using the Vectastain Elite ABC Kit™ (Vector Laboratories™) and stable DAB (diaminobenzidine and H2O2; Research Genetics™). Staining was performed using the DAKO Autostainer™ at room temperature.

Results

IHC staining of human cancer using an antibody specific to the extracellular domain of LFL2 (mAb #192) demonstrated strong LFL2 protein expression in the stroma of cancers of the lung, breast, colon, ovaries, and pancreas. No LFL2 staining was detected in renal cell carcinomas.

More specifically in lung tissue, LFL2 expression was detected in the desmoplastic stroma of 13/15 lung adeno- and squamous cell carcinoma. No staining was detected in the carcinoma cells or in the normal interstitial fibroblasts in normal lung.

In colon tissue, strong staining for LFL2 was detected in stroma of 14/14 colon cancer samples, but not in the cancer epithelia nor in normal colon tissue.

In breast tissue, strong LFL2 staining was detected in desmoplastic stroma of 9/9 breast cancer samples. No staining was detected in cancer epithelial cells.

In ovarian tissue, strong immunostaining for LFL2 was observed in stroma associated with 4/4 omental metastatic ovarian cancers. No staining was detected in adjacent omentum.

In addition, no IHC staining was detected in normal liver and normal pancreas. These results confirm the results of the gene microarray studies that indicated LFL2 is up-regulated in a select set of cancer indications. In addition, these IHC results demonstrate that LFL2 is a cancer-stroma specific gene and is not expressed in cancer epithelia, normal stroma or other normal tissues tested.

Example 4

In Vivo Induction of Murine LFL2 Protein by Human Cancer Xenografts

IHC Analysis of Human Cancer Xenografts

Human cancer cell lines derived from multiple cancers were implanted subcutaneously under the right flanks of CB-17 SCID mice to generate xenograft tumors. Tumors were allowed to establish until reaching an average of 200-500 $mm^3$ as determined by caliper measurement and calculated by π/6×length×width×height. Tumor volume was measured twice weekly and clinical and mortality observations were performed daily according to IACUC regulations. Harvested xenograft tumors were frozen in OCT compound and were processed for IHC as described in Example 3. Immunostaining of murine LFL2 was accomplished using anti-LFL2 mAb M25, which recognizes both human and murine LFL2 protein.

In Vivo Imaging of Murine LFL2

Human BxPC3 pancreatic xenografts were grown in mice as described above. Tumors were allowed to reach at least 200 $mm^3$ in size. Anti-LFL2 mAb M25 was labeled with Alexa488™. The labeled mAb was injected intravenously or intra-peritoneally into tumor bearing mice. Two hours post-injection, tumors were harvested and were analyzed for: (1) total LFL2 protein expression using IHC; (2) in vivo accessible LFL2 protein by either staining sections only with secondary antibody to detect M25 localization to the tumor stroma, or by direct view on frozen sections using fluorescence microscopy to detect Alexa488™ staining.

Results

To develop in vivo model systems to investigate LFL2 function, human cancer xenografts were grown subcutaneously in SCID mice. The cancer cell lines used to generate the xenograft tumors included: A549 (lung adenocarcinoma), ES2 (ovarian cancer), MW231 (breast cancer), HCT116 (colon cancer), BxPC3 (pancreatic cancer) and LNCaP (prostate cancer). IHC analysis of these tumors using anti-LFL2 mAb M25 showed that none of the human cancer cells express LFL2 protein. However, LFL2 protein expression was detected in tumor-associated stroma in response to the human tumors xenografted in the SCID mice. More specifically, murine LFL2 protein was induced in mouse stromal cells in response to A549 (lung adenocarcinoma), ES2 (ovarian cancer), MW231 (breast cancer), HCT116 (colon cancer) and BxPC3 (pancreatic cancer) cell lines, but not in response to LNCaP (prostate cancer) cells. Murine LFL2 was not detected in normal mouse tissues including: spleen, brain, small intestine, kidney, lung, pancreas, liver and heart. These observations correlate with the IHC results of clinical human cancer specimens, in which expression of LFL2 is detected in cancers of the lung, ovary, colon, and pancreas, but not in prostate cancer or in normal tissues.

To determine if murine LFL2 in the BxPC3 associated stroma is accessible to anti-LFL2 antibodies in the circulation, an in vivo imaging experiment was performed. The results show that within 2 hours of injecting fluorescently labeled anti-LFL2 mAb M25, specific mAb staining can be visualized only in the tumor stroma. This demonstrates that LFL2 protein on tumor stroma is accessible to therapeutic anti-LFL2 antibodies present in the circulation.

Example 5

In Vitro Induction of LFL2 Protein by Human Cancer Cells and by TGFβ1

Co-Culturing, TGFβ1 Treatment and Flow Cytometry Analysis

For co-culturing assays, human cancer cell lines (MB231, A253, H23) were co-cultured on plastic with murine fibroblast cell lines (CL7, 3T12, 3T3) at a 1:1 ratio for 3 days. For transforming growth-factor β1 (TGFβ1) mediated induction of LFL2, human (CCD8, IMR90) and mouse (CL7) fibroblast cell lines were treated with 10 ng/ml of TGFβ1 for 24 hours. To measure LFL2 protein induction on the cell surface, cells were removed with 5 mM EDTA in Tris-HCl (pH 8.0) and blocked by centrifugation in Hank's balanced salt solution containing 3% heat inactivated FBS, 1% normal goat serum (Sigma-Aldrich™, St. Louis, Mo.) and 1% BSA at 4° C. for 5 minutes. Cells were incubated for 30-60 minutes at 4° C. with primary mAb (negative control antibody, anti-human LFL2 mAb #139, or anti-mouse and -human LFL2 mAb M25) at 10 μg/ml in FACS buffer (PBS containing 0.1% BSA). After washing in FACS buffer, cells were re-suspended in Cy5-anti-mouse IgG (H+L) antibody (Caltag Laboratories™, Burlingame, Calif., 1:50 dilution) for 30-60 minutes at 4° C. Cells were washed and re-suspended in FACS buffer containing propidium iodide (1 μg/ml). Fluorescence intensity was measured on a FACScan (BD Biosciences™, San Jose, Calif.).

Results

LFL2 protein is expressed in cancer stroma of clinical tissue specimens and in murine stroma associated with human cancer xenografts. This suggests that human cancer cells induce LFL2 protein expression in stroma by direct contact or by secretion of an inducing factor that binds to a stromal receptor. To confirm this theory, human and mouse fibroblast cell lines were co-cultured in the presence of human cancer cell lines. FACS analysis using anti-LFL2 mAb M25 shows that LFL2 protein is induced in cells within 3 days of co-culturing. M25 recognizes both murine and human LFL2, while mAb#139 only recognizes human LFL2. Since only M25 detected LFL2 induction, while mAb#139 did not, one can deduce that LFL2 protein was induced in the murine fibroblasts, rather than in the human cancer cells. More specifically, based on mean fluorescence intensity, murine LFL2 was induced 200% in CL7 cells, 80% in 3T12 cells, and 50% in 3T3 cells. The mechanism of this induction by cancer cells is unknown. However, several factors that induce stromal cell changes during tumor cell growth include TGFβ1 (Sieweke et al., Science, 1990; 248:1656-60).

TGFβ1 is a multifunctional peptide that controls proliferation, differentiation, and other functions in many normal and cancerous cell types (Sporn et al., Science, 1986; 233:532-4; Roberts and Wakefield, Proc Natl Acad Sci USA, 2003; 100: 8621-3; Siegel and Massague, Nature Reviews Cancer, 2003; 3, 807-20). TGFβ was originally identified as a factor capable of transforming normal fibroblasts into malignant cells (Sporn et al., Science, 1986; 233:532-4). However, subsequent research showed that TGFβ, under normal conditions, functions as a tumor suppressor and controls cell and tissue growth by controlling the expression of cell cycle regulators (Chen et al., Proc. Natl. Acad. Sci. USA, 2001; 98: 992-9). Tumor cells often acquire resistance to TGFβ-mediated growth control, and even overproduce this factor, leading to a local immunosuppressive environment that fosters tumor growth and intensifies the invasive and metastatic potential of the tumor cells (Siegel and Massague, Nature Reviews Cancer, 2003; 3, 807-20). One mechanism by which TGFβ may increase cancer cell invasiveness is via its influence on the tumor stroma (De Weever and Mareel, J Pathol., 2003; 200: 429-47). TGFβ is one of the factors that induce the transdifferentiation of fibroblasts into myofibroblasts, which are a characteristic of stromal cell changes that occur during cancer cell invasion (De Weever and Mareel, J Pathol., 2003; 200: 429-47).

To determine if TGFβ1 can modulate LFL2 expression, murine (CL7) and human (CCD8, IMR90) stromal fibroblast cell lines were treated with TGFβ1. After 24 hours FACS analysis using mAb M25 was performed and the results show a significant increase in LFL2 cell surface protein expression in treated fibroblasts compared to mock treated cells. More specifically, based on mean fluorescence intensity, LFL2 was induced 3-4 fold in CL7 cells, 2 fold in CCD8 cells, and 2 fold in IMR90 cells. These data demonstrate that LFL2 is at least in part a TGFβ1-regulated gene. It also suggests that cancer stroma expression of LFL2 may also be in part due to the action of TGFβ1 secretion by adjacent tumor cells.

Example 6

In Vitro Killing by Toxin-Conjugated Anti-LFL2 mAb

Immunofluorescence and Internalization Assay

3T3 and 3T3-LFL2 cells grown on cover slips were incubated with medium containing anti-LFL2 mAb M25 (5 μg/ml) at 4° C. for 1 h. Antibody binding was detected using AlexaFluor-488™ goat anti-mouse secondary antibody (1:2200 dilution) (Invitrogen—Molecular Probes™, Eugene, Oreg.). Cells were washed and fixed using 5% UltraPure Formaldehyde™ in PBS for 40 min. Slides were mounted using Permafluor™ (Beckman-Coulter™, Miami, Fla.) for visualization. For internalization, cells were placed in an incubator at 37° C. for 1 h and then placed on ice for 1 h in blocking solution (20 μg/ml pure goat anti-mouse antibody in media). After washing in PBS, cells were fixed in 5% ultra pure formaldehyde. Cells were then washed with 0.5% Triton X-100™ and incubated with AlexaFluor-594™ goat anti-mouse secondary antibody (1:2200) (Invitrogen—Molecular Probes™, Eugene, Oreg.). Staining was visualized with a Nikon E800™ fluorescence microscope.

Antibody-Drug Conjugate (ADC) Chemistry

Purified anti-LFL2 mAb M25 or control murine IgG1 TIB191 were conjugated to valine-citrulline-monomethyl auristatin E (maleimide-vcMMAE, Seattle Genetics™) as described by Bhaskar et al. (Cancer Res, 2003; 63: 6387-94). Purified antibody (either M25 or control murine IgG2a) was reduced with 10 mM DTT. Thiol content was determined by measuring $A_{412}$ after incubation with Ellman's™ reagent and subsequent calculation. Equimolar maleimide-vcMMAE solution (8 mM in DMSO) in cold acetonitrile (20% final concentration) was incubated with reduced mAb for 30 minutes at 4° C. Unconjugated vcMMAE was removed by dialysis at 4° C. into PBS and filtered. Conjugated mAb was quantified using $A_{280}/A_{260}$ and the extent of aggregate vs. monomer was determined by size-exclusion HPLC. Finally, MALDI-TOF was used to determine the number of drug molecules per mAb.

In Vitro Growth Assays

Parental and LFL2 transfected 3T3 cell lines were plated at a density of 2500 cells/well in 96-well plates and were allowed to recover overnight in phenol-free IMDM containing 10% FBS and supplements (growth medium). Cell growth in the presence of ADC was determined as described by Bhaskar et al. (Cancer Res, 2003; 63: 6387-94). Cells were challenged for 1 hour with mAb or ADC in IMDM at the indicated concentrations. Cells were then washed twice with growth medium and allowed to proliferate in fresh growth medium for 4 days. Cell viability was assessed using the CellTiter 96 AQueous Non-Radioactive Cell Proliferation Assay™ (Promega Biosciences™, San Luis Obispo, Calif.). All growth studies were done at least 3 times in triplicate.

Results

To assess LFL2 as an ADC target for the killing of cancer cells, it was first determined that anti-LFL2 mAbs internalize after binding LFL2 on the cell surface. M25 internalized into subcellular compartments starting with 4 hours after binding to LFL2 on the surface of 3T3-LFL2 cells. Internalization was complete after 24 hours of incubation. This internalization time course is significantly slower compared to other ADC targets, which internalize completely within 2 hours of incubation (Afar et al., Mol Cancer Ther. 3(8):921-32 (2004)). This slower rate of internalization would allow for both an ADC and an antibody-dependent cellular cytotoxicity (ADCC) approach, for which the antigen-mAb complex is required to reside on the cell surface for longer periods of time. In ADCC, an un-conjugated naked antibody is used to recruit immune effector cells to the tumor, which then kill the targeted tumor cells.

Anti-LFL2 mAbs #139 and M25 were conjugated to the microtubule toxin auristatin E through a cathepsin B-cleavable linker (Doronina et al., Nat Biotechnol, 2003; 21: 778-84) designed to limit toxicity to cells that internalize the target-ADC complex to lysosomes. Both ADCs were toxic to 3T12-LFL2 transfectants at an IC50 of 0.1 ug/ml and U118 glioblastoma cells at an IC50 of 0.5 μg/ml. In addition, human IMR90 fibroblasts that were induced to express LFL2 after stimulation with TGFβ1 were also killed with anti-LFL2 ADC at an IC50 of 1-2 μg/ml. These results demonstrate that anti-LFL2 ADCs can specifically target and kill LFL2-expressing cells.

Example 7

Shedding of LFL2 from the Cell Surface of Cells

LFL2 Protein Detection Protocols

To detect LFL2 protein in cells 3T12-LFL2 cells were passaged in tissue culture as described above. Cell lysates were prepared in SDS-PAGE sample buffer and 50 μg of cell lysate protein were analyzed by Western blotting using anti-HA antibodies at 1 μg/ml. To detect clipped LFL2 protein, tissue culture supernatants were collected from 3T12-LFL2 cells and U118 cells. Conditioned media (10 ml) was concentrated to 1 ml and LFL2 protein was immunoprecipitated using either M25 or anti-LFL2 #139 mAbs at 5 μg/ml. Immunoprecipitated LFL2 protein was then detected by Western blotting using anti-LFL2 mAb D26.

For capture ELISAs anti-LFL2 mAbs #139 or M25 were coated onto 96 well plates at 1 μg/ml overnight at 4° C. in sodium bicarbonate buffer, pH 9.6. Fifty μl of concentrated cell supernatant was added to the wells for 2 hours at room temperature. Secondary biotinylated anti-mouse IgG was then added at room temperature for 1 hour, followed by incubation with streptavidin HRP (horse-radish peroxidase) for 1 hour at room temperature. The HRP substrate TMB (tetra-methyl benzidine) was then added for 10 minutes and the signal was detected spectrophotometrically at OD650.

Generation of Antibodies Towards the LFL2 Extracellular Stub Region

Mice were immunized with a polypeptide with the following amino acid sequence corresponding to amino acid residues 527-538 of the full length LFL2 sequence: SVWGMTQAQS (SEQ ID NO: 6). Antibody methods were performed as described above. A panel of anti-LFL2 stub-region specific antibodies were identified using a variety of techniques including Western blotting and FACS analysis of LFL2-expressing cell lines.

Results

Examination of the LFL2 protein sequence revealed a potential proteolytic cleavage site in the extracellular domain located between residues 527 and 528 of SEQ ID NO:1. Clipping of LFL2 protein at that site would result in the shedding of the bulk of the LFL2 protein from the cell surface of cells with a small protein stump, or stub region, of about 10 amino acids in length left at the cell surface.

To determine if LFL2 protein is shed, cell lysates of 3T12-LFL2 were analyzed by Western blotting using an anti-HA antibody, which recognizes the carboxyl-terminus of the HA-tagged LFL2 protein. The Western blotting results revealed 2 protein species, one predicted to be the size of full length LFL2 (~60 kD) and the other one predicted to be the size of LFL2 protein after clipping of the extracellular region (~6 kD). This data suggested that LFL2 is in part proteolytically cleaved at the cell surface. To confirm this result, conditioned media from 3T12 LFL2 cells and from U118 glioblastoma cells, which endogenously express LFL2, were analyzed for LFL2 protein. The results showed that anti-LFL2 immunoprecipitates from conditioned media contained detectable amounts of LFL2 protein. Similarly, a capture ELISA designed to identify LFL2 protein in solution at a sensitivity of 1 ng/ml also detected LFL2 protein in the supernatants of cells that express LFL2. This capture ELISA may be useful in the detection of LFL2 protein in blood samples of cancer patients.

These results demonstrate that LFL2 is, in part, shed from the cell surface by proteolytic cleavage. This also suggests that patients that have LFL2 positive cancers may exhibit certain levels of LFL2 protein in their blood. This makes LFL2 a potentially important biomarker for the diagnosis of cancer and monitoring of disease progression. LFL2 may be used to initially diagnose a cancer, before it becomes symptomatic. Such diagnostics are especially important for rapidly growing tumors such as pancreatic cancer. LFL2 may also be important in monitoring disease progression after a diagnosis has been made. In addition, LFL2 may be used as a biomarker to monitor treatment efficacy, i.e. if a treatment is effective, the levels of LFL2 protein in the blood may decrease. Alternatively, an increase in blood levels of LFL2 may signify that a treatment is ineffective.

Shedding of the extracellular region of LFL2 corresponding to amino acids 24-527 of SEQ ID NO:1 leaves behind a protein stub region at the cell surface with the following amino acid sequence: SVWGMTQAQS (SEQ ID NO: 6). This protein fragment may be accessible to potential therapeutic antibodies at the cell surface of target cells. Using a peptide immunogen that contains the stub region sequence, a panel of antibodies was generated. Two mAbs, clones 1-19G12 and 1-13C3, specifically recognize full length and the clipped LFL2 stub region by FACS analysis of 3T12-LFL2 cells on the cell surface. Both mAbs also recognize a protein of the predicted molecular weight (~6 kD) by Western blotting. These stub region recognizing antibodies, as well as others with the same binding specificity, can be used as ADCs or in ADCC to specifically target LFL2 expressing cells for killing even after shedding has occurred.

It is understood that the examples described above in no way serve to limit the true scope of this invention, but rather are presented for illustrative purposes. All publications, sequences of accession numbers, and patent applications cited in this specification are herein incorporated by reference as if each individual publication or patent application were specifically and individually indicated to be incorporated by reference.

All UniGene cluster identification numbers and accession numbers herein are for the GenBank sequence database and the sequences of the accession numbers are hereby expressly incorporated by reference. GenBank is known in the art, see, e.g., Benson, D A, et al., Nucleic Acids Research 26:1-7 (1998). Sequences are also available in other databases, e.g., European Molecular Biology Laboratory (EMBL) and DNA Database of Japan (DDBJ).

Deposit of Material

The following material has been deposited with the American Type Culture Culture Collection, 10801 University Blvd., Manassas, Va. 20110-2209, USA (ATCC):

| Material | ATCC Patent Deposit Designation No. | Deposit Date |
|---|---|---|
| Murine Hybridoma: LFL2 #139 (produces anti-LFL2 mAb #139)) | PTA-6163 | Aug. 24, 2004 |
| Murine Hybridoma: 1-19 G12 (produces anti-LFL2 mAB 1-19 G12) | PTA-6256 | Oct. 15, 2004 |
| Murine Hybridoma: 1-13C3 (produces anti-LFL2 mAB 1-13C3 | PTA-6330 | Nov. 22, 2004 |

This deposit was made under the provisions of the Budapest Treaty on the International Recognition of the Deposit of Microorganisms for the purpose of Patent Procedure and the Regulations thereunder (Budapest Treaty). This assures maintenance of a viable culture of the deposit for 30 years from the date of deposit. The deposit will be made available by ATCC under the terms of the Budapest Treaty, and subject to an agreement between Protein Design Labs, Inc. and ATCC, which assures permanent and unrestricted availability of the progeny of the culture of the deposit to the public upon influence of the pertinent U.S. patent or upon laying open to the public of any U.S. or foreign patent application, whichever comes first, and assures availability of the progeny to one determined by the U.S. Commissioner of Patents and Trade to be entitled thereto according to 35 U.S.C. § 122 and the Commissioner's rules pursuant thereto (including 37 CFR § 1.14 with particular reference to 886 OG 638)

The assignee of the present application has agreed that if a culture of the materials on deposit should die or be lost or destroyed when cultivated under suitable conditions, the materials will be promptly replaced on notification with another of the same. Availability of the deposited material is not to be construed as a license to practice the invention in contravention of the right granted under the authority of any government in accordance with its patent laws.

The present invention should not to be limited in scope by the construct deposited, since the deposited embodiment is intended as a single illustration of certain aspects of the invention and any constructs that are functionally equivalent are within the scope of the this invention.

What is claimed is:

1. A method for inhibiting proliferation of a cancer cell comprising contacting the cancer cell with an antibody that specifically binds to SEQ ID NO: 1 or SEQ ID NO: 6, wherein the antibody is selected from the group consisting of: an antibody having a heavy chain variable region amino acid sequence of SEQ ID NO: 3 and a light chain variable region amino acid sequence of SEQ ID NO: 5, an antibody produced by the hybridoma cell line deposited as ATCC Accession No. PTA-6163, an antibody produced by the hybridoma cell line deposited as ATCC Accession No. PTA-6256, and an antibody produced by the hybridoma cell line deposited as ATCC Accession No. PTA-6330.

2. The method of claim 1, wherein the cancer cell is selected from the group consisting of: a breast, head/neck, lung, ovarian, stomach and pancreatic cancer cell.

3. The method of claim 1, wherein the antibody is conjugated to a cytotoxic agent.

4. The method of claim 3, wherein the cytotoxic agent is auristatin E or auristatin F.

5. The method of claim 1, wherein the cancer cell is TGF-beta positive.

6. A method for slowing the development of cancer comprising contacting a cancer cell with an antibody that specifically binds to SEQ ID NO: 1 or SEQ ID NO: 6, wherein the antibody is selected from the group consisting of: an antibody a heavy chain variable region amino acid sequence of SEQ ID NO: 3 and a light chain variable region amino acid sequence of SEQ ID NO: 5, an antibody produced by the hybridoma cell line deposited as ATCC Accession No. PTA-6163, an antibody produced by the hybridoma cell line deposited as ATCC Accession No. PTA-6256, and an antibody produced by the hybridoma cell line deposited as ATCC Accession No. PTA-6330.

7. The method of claim 6 wherein the cancer cell is selected from the group consisting of: a breast, head/neck, lung, ovarian, stomach and pancreatic cancer cell.

8. The method of claim 6, wherein the cancer cell is TGF-beta positive.

9. The method of claim 6, wherein the antibody is conjugated to a cytotoxic agent.

10. The method of claim 9, wherein the cytotoxic agent is auristatin E.

* * * * *

SEQUENCE LISTING

```
<160> NUMBER OF SEQ ID NOS: 15

<210> SEQ ID NO 1
<211> LENGTH: 581
<212> TYPE: PRT
<213> ORGANISM: Homo sapiens

<400> SEQUENCE: 1

Met Pro Leu Lys His Tyr Leu Leu Leu Leu Val Gly Cys Gln Ala Trp
1               5                   10                  15

Gly Ala Gly Leu Ala Tyr His Gly Cys Pro Ser Glu Cys Thr Cys Ser
            20                  25                  30

Arg Ala Ser Gln Val Glu Cys Thr Gly Ala Arg Ile Val Ala Val Pro
        35                  40                  45

Thr Pro Leu Pro Trp Asn Ala Met Ser Leu Gln Ile Leu Asn Thr His
    50                  55                  60

Ile Thr Glu Leu Asn Glu Ser Pro Phe Leu Asn Ile Ser Ala Leu Ile
65                  70                  75                  80

Ala Leu Arg Ile Glu Lys Asn Glu Leu Ser Arg Ile Thr Pro Gly Ala
                85                  90                  95

Phe Arg Asn Leu Gly Ser Leu Arg Tyr Leu Ser Leu Ala Asn Asn Lys
            100                 105                 110

Leu Gln Val Leu Pro Ile Gly Leu Phe Gln Gly Leu Asp Ser Leu Glu
        115                 120                 125

Ser Leu Leu Leu Ser Ser Asn Gln Leu Leu Gln Ile Gln Pro Ala His
    130                 135                 140

Phe Ser Gln Cys Ser Asn Leu Lys Glu Leu Gln Leu His Gly Asn His
145                 150                 155                 160

Leu Glu Tyr Ile Pro Asp Gly Ala Phe Asp His Leu Val Gly Leu Thr
                165                 170                 175

Lys Leu Asn Leu Gly Lys Asn Ser Leu Thr His Ile Ser Pro Arg Val
            180                 185                 190

Phe Gln His Leu Gly Asn Leu Gln Val Leu Arg Leu Tyr Glu Asn Arg
        195                 200                 205

Leu Thr Asp Ile Pro Met Gly Thr Phe Asp Gly Leu Val Asn Leu Gln
    210                 215                 220

Glu Leu Ala Leu Gln Gln Asn Gln Ile Gly Leu Leu Ser Pro Gly Leu
225                 230                 235                 240

Phe His Asn Asn His Asn Leu Gln Arg Leu Tyr Leu Ser Asn Asn His
                245                 250                 255

Ile Ser Gln Leu Pro Pro Ser Ile Phe Met Gln Leu Pro Gln Leu Asn
            260                 265                 270

Arg Leu Thr Leu Phe Gly Asn Ser Leu Lys Glu Leu Ser Leu Gly Ile
        275                 280                 285

Phe Gly Pro Met Pro Asn Leu Arg Glu Leu Trp Leu Tyr Asp Asn His
    290                 295                 300

Ile Ser Ser Leu Pro Asp Asn Val Phe Ser Asn Leu Arg Gln Leu Gln
305                 310                 315                 320

Val Leu Ile Leu Ser Arg Asn Gln Ile Ser Phe Ile Ser Pro Gly Ala
                325                 330                 335

Phe Asn Gly Leu Thr Glu Leu Arg Glu Leu Ser Leu His Thr Asn Ala
            340                 345                 350

Leu Gln Asp Leu Asp Gly Asn Val Phe Arg Met Leu Ala Asn Leu Gln
```

-continued

```
        355                 360                 365

Asn Ile Ser Leu Gln Asn Asn Arg Leu Arg Gln Leu Pro Gly Asn Ile
    370                 375                 380

Phe Ala Asn Val Asn Gly Leu Met Ala Ile Gln Leu Gln Asn Asn Gln
385                 390                 395                 400

Leu Glu Asn Leu Pro Leu Gly Ile Phe Asp His Leu Gly Lys Leu Cys
                405                 410                 415

Glu Leu Arg Leu Tyr Asp Asn Pro Trp Arg Cys Asp Ser Asp Ile Leu
            420                 425                 430

Pro Leu Arg Asn Trp Leu Leu Leu Asn Gln Pro Arg Leu Gly Thr Asp
        435                 440                 445

Thr Val Pro Val Cys Phe Ser Pro Ala Asn Val Arg Gly Gln Ser Leu
    450                 455                 460

Ile Ile Ile Asn Val Asn Val Ala Val Pro Ser Val His Val Pro Glu
465                 470                 475                 480

Val Pro Ser Tyr Pro Glu Thr Pro Trp Tyr Pro Asp Thr Pro Ser Tyr
                485                 490                 495

Pro Asp Thr Thr Ser Val Ser Ser Thr Thr Glu Leu Thr Ser Pro Val
            500                 505                 510

Glu Asp Tyr Thr Asp Leu Thr Thr Ile Gln Val Thr Asp Asp Arg Ser
        515                 520                 525

Val Trp Gly Met Thr Gln Ala Gln Ser Gly Leu Ala Ile Ala Ala Ile
    530                 535                 540

Val Ile Gly Ile Val Ala Leu Ala Cys Ser Leu Ala Ala Cys Val Gly
545                 550                 555                 560

Cys Cys Cys Cys Lys Lys Arg Ser Gln Ala Val Leu Met Gln Met Lys
                565                 570                 575

Ala Pro Asn Glu Cys
            580


<210> SEQ ID NO 2
<211> LENGTH: 414
<212> TYPE: DNA
<213> ORGANISM: Mus musculus

<400> SEQUENCE: 2

atggattgga cctgggtctt tctcttcctc ctgtcagtaa ctgcaggggt ccactcccag     60

gttcagctgc agcagtctgg agctgaactg atgaagcctg gggcctcagt gaagatatcc    120

tgcaaggcta ctggctacaa attcagtagt tactggatag agtgggtaaa gcagaggcct    180

ggacatggcc ttgagtggat tggagagatt ttacctggaa gtgatactac taactacaat    240

gagaagttca aggacaaggc cacattcact tcagatacat cctccaacac agcctacatg    300

caactcagca gcctgacatc tgaggactct gccgtctatt attgtgcaag agaccgtggt    360

aactaccggg cctggtttgg ttactggggc caggggactc tggtcactgt ctct          414


<210> SEQ ID NO 3
<211> LENGTH: 138
<212> TYPE: PRT
<213> ORGANISM: Mus musculus

<400> SEQUENCE: 3

Met Asp Trp Thr Trp Val Phe Leu Phe Leu Leu Ser Val Thr Ala Gly
1               5                   10                  15

Val His Ser Gln Val Gln Leu Gln Gln Ser Gly Ala Glu Leu Met Lys
            20                  25                  30
```

-continued

```
Pro Gly Ala Ser Val Lys Ile Ser Cys Lys Ala Thr Gly Tyr Lys Phe
        35                  40                  45

Ser Ser Tyr Trp Ile Glu Trp Val Lys Gln Arg Pro Gly His Gly Leu
    50                  55                  60

Glu Trp Ile Gly Glu Ile Leu Pro Gly Ser Asp Thr Thr Asn Tyr Asn
65                  70                  75                  80

Glu Lys Phe Lys Asp Lys Ala Thr Phe Thr Ser Asp Thr Ser Ser Asn
                85                  90                  95

Thr Ala Tyr Met Gln Leu Ser Ser Leu Thr Ser Glu Asp Ser Ala Val
            100                 105                 110

Tyr Tyr Cys Ala Arg Asp Arg Gly Asn Tyr Arg Ala Trp Phe Gly Tyr
        115                 120                 125

Trp Gly Gln Gly Thr Leu Val Thr Val Ser
    130                 135


<210> SEQ ID NO 4
<211> LENGTH: 381
<212> TYPE: DNA
<213> ORGANISM: Mus musculus

<400> SEQUENCE: 4

atgatgtcct ctgctcagtt ccttggtctc ctgttgctct gttttcaagg tatcagatgt      60

gatatccaga tgacacagac atcctccctg tctgcctctc tgggagacag agtcaccatc     120

agttgcaggg caagtcagga cattagcaat tatttaaact ggtatcagca gaaaccagat     180

ggaactgtta aattcctaat ctactacaca tcaagattac actcaggagt cccatcaagg     240

ttcagtggca gtgggtctgg aacagattat tctctcacca ttagctacct ggagccagaa     300

gatattgcca catactttg ccaacagggt gaagcgcttc cgtggacgtt cggtggaggc     360

accaagctgg aaatcaaacg g                                               381


<210> SEQ ID NO 5
<211> LENGTH: 127
<212> TYPE: PRT
<213> ORGANISM: Mus musculus

<400> SEQUENCE: 5

Met Met Ser Ser Ala Gln Phe Leu Gly Leu Leu Leu Leu Cys Phe Gln
1               5                   10                  15

Gly Ile Arg Cys Asp Ile Gln Met Thr Gln Thr Ser Ser Leu Ser Ala
            20                  25                  30

Ser Leu Gly Asp Arg Val Thr Ile Ser Cys Arg Ala Ser Gln Asp Ile
        35                  40                  45

Ser Asn Tyr Leu Asn Trp Tyr Gln Gln Lys Pro Asp Gly Thr Val Lys
    50                  55                  60

Phe Leu Ile Tyr Tyr Thr Ser Arg Leu His Ser Gly Val Pro Ser Arg
65                  70                  75                  80

Phe Ser Gly Ser Gly Ser Gly Thr Asp Tyr Ser Leu Thr Ile Ser Tyr
                85                  90                  95

Leu Glu Pro Glu Asp Ile Ala Thr Tyr Phe Cys Gln Gln Gly Glu Ala
            100                 105                 110

Leu Pro Trp Thr Phe Gly Gly Gly Thr Lys Leu Glu Ile Lys Arg
        115                 120                 125


<210> SEQ ID NO 6
<211> LENGTH: 10
```

-continued

<212> TYPE: PRT
<213> ORGANISM: Homo sapiens

<400> SEQUENCE: 6

Ser Val Trp Gly Met Thr Gln Ala Gln Ser
1 5 10

<210> SEQ ID NO 7
<211> LENGTH: 25
<212> TYPE: DNA
<213> ORGANISM: Artificial
<220> FEATURE:
<223> OTHER INFORMATION: Oligonucleotide

<400> SEQUENCE: 7
aggttctgcc catcggcctc ttcca 25

<210> SEQ ID NO 8
<211> LENGTH: 27
<212> TYPE: DNA
<213> ORGANISM: Artificial
<220> FEATURE:
<223> OTHER INFORMATION: Oligonucleotide

<400> SEQUENCE: 8
atgccactga agcattatct ccttttg 27

<210> SEQ ID NO 9
<211> LENGTH: 24
<212> TYPE: DNA
<213> ORGANISM: Artificial
<220> FEATURE:
<223> OTHER INFORMATION: Oligonucleotide

<400> SEQUENCE: 9
tgctccagcc tgcctcttta acac 24

<210> SEQ ID NO 10
<211> LENGTH: 36
<212> TYPE: DNA
<213> ORGANISM: Artificial
<220> FEATURE:
<223> OTHER INFORMATION: Oligonucleotide

<400> SEQUENCE: 10
tggttaatta acatgccact gaagcattat ctcctt 36

<210> SEQ ID NO 11
<211> LENGTH: 32
<212> TYPE: DNA
<213> ORGANISM: Artificial
<220> FEATURE:
<223> OTHER INFORMATION: Oligonucleotide

<400> SEQUENCE: 11
attgcggccg ccccgctctg ggcctgggtc at 32

<210> SEQ ID NO 12
<211> LENGTH: 22
<212> TYPE: DNA
<213> ORGANISM: Artificial
<220> FEATURE:
<223> OTHER INFORMATION: Oligonucleotide

<400> SEQUENCE: 12
atgctgcagt cttgagccgg tc 22

-continued

```
<210> SEQ ID NO 13
<211> LENGTH: 23
<212> TYPE: DNA
<213> ORGANISM: Artificial
<220> FEATURE:
<223> OTHER INFORMATION: Oligonucleotide

<400> SEQUENCE: 13

ttatgtggcc ccaggtttgg aag                                          23


<210> SEQ ID NO 14
<211> LENGTH: 34
<212> TYPE: DNA
<213> ORGANISM: Artificial
<220> FEATURE:
<223> OTHER INFORMATION: Oligonucleotide

<400> SEQUENCE: 14

aggttaatta agatgccgct gaaacattat ctcc                              34


<210> SEQ ID NO 15
<211> LENGTH: 35
<212> TYPE: DNA
<213> ORGANISM: Artificial
<220> FEATURE:
<223> OTHER INFORMATION: Oligonucleotide

<400> SEQUENCE: 15

atgcggccgc ttcgatggtg tttagatcgg tgtag                             35
```